(12) United States Patent
Fezza et al.

(10) Patent No.: US 12,303,676 B2
(45) Date of Patent: May 20, 2025

(54) COMBINED NEEDLE AND CANNULA

(71) Applicant: Arya Medical, Inc., Menlo Park, CA (US)

(72) Inventors: John P. Fezza, Osprey, FL (US); Felix Vega, San Francisco, CA (US); Darrin James Kent, Murrieta, CA (US); David James Prince, Saint Paul, MN (US)

(73) Assignee: Arya Medical, Inc., Menlo Park, CA (US)

( * ) Notice: Subject to any disclaimer, the term of this patent is extended or adjusted under 35 U.S.C. 154(b) by 930 days.

(21) Appl. No.: 17/241,289

(22) Filed: Apr. 27, 2021

(65) Prior Publication Data

US 2021/0330896 A1    Oct. 28, 2021

Related U.S. Application Data

(60) Provisional application No. 63/092,855, filed on Oct. 16, 2020, provisional application No. 63/015,981, filed on Apr. 27, 2020.

(51) Int. Cl.
| | |
|---|---|
| *A61M 5/32* | (2006.01) |
| *A61L 27/12* | (2006.01) |
| *A61L 27/18* | (2006.01) |
| *A61L 27/20* | (2006.01) |

(52) U.S. Cl.
CPC .......... *A61M 5/3271* (2013.01); *A61L 27/12* (2013.01); *A61L 27/18* (2013.01); *A61L 27/20* (2013.01); *A61M 5/3234* (2013.01); *A61M 2005/3201* (2013.01)

(58) Field of Classification Search
None
See application file for complete search history.

(56) References Cited

U.S. PATENT DOCUMENTS

| | | | | |
|---|---|---|---|---|
| 3,840,008 | A * | 10/1974 | Noiles | A61M 5/3287 604/117 |
| 4,627,841 | A * | 12/1986 | Dorr | A61M 25/0637 604/165.03 |
| 5,312,372 | A * | 5/1994 | DeHarde | A61M 5/3275 604/110 |
| 6,623,456 | B1 * | 9/2003 | Holdaway | A61M 25/0643 604/164.08 |

(Continued)

OTHER PUBLICATIONS

PCT International Search Report and Written Opinion in International Application PCT/US2021/029366, mailed Aug. 9, 2021, 16 pages.

*Primary Examiner* — Manuel A Mendez
(74) *Attorney, Agent, or Firm* — Merchant & Gould P.C.

(57) ABSTRACT

A device for performing injections in a patient includes a syringe holder with a needle guard, a cannula extending from the syringe holder, a needle slidably disposed over the cannula, and a slider on the syringe holder. The cannula has a blunt tip and a cannula length, and the needle has a sharp tip and a needle length that is shorter than the cannula length. The slider is coupled with the needle and is configured to slide the needle along the cannula from an extended position, in which the sharp tip of the needle is located at or immediately adjacent the blunt tip of the cannula, to a retracted position, in which the sharp tip is housed within the needle guard of the syringe holder.

13 Claims, 38 Drawing Sheets

(56) References Cited

U.S. PATENT DOCUMENTS

| | | | | |
|---|---|---|---|---|
| 6,716,199 B2* | 4/2004 | DeHarde | ............ | A61M 5/3269 |
| | | | | 604/110 |
| 7,077,824 B2* | 7/2006 | Meyer | ................ | A61M 5/5066 |
| | | | | 604/110 |
| 7,115,111 B2* | 10/2006 | Haindl | .............. | A61M 25/0631 |
| | | | | 604/164.01 |
| 7,361,159 B2* | 4/2008 | Fiser | .................. | A61M 5/3275 |
| | | | | 604/192 |
| 10,286,161 B2 | 5/2019 | Persons | | |
| 10,322,264 B2 | 6/2019 | Chuang et al. | | |
| 2007/0106213 A1* | 5/2007 | Spera | .................. | A61M 31/00 |
| | | | | 604/915 |
| 2011/0071476 A1 | 3/2011 | Mueller | | |
| 2018/0117263 A1 | 5/2018 | Cumbo | | |
| 2019/0275262 A1 | 9/2019 | Persons | | |

\* cited by examiner

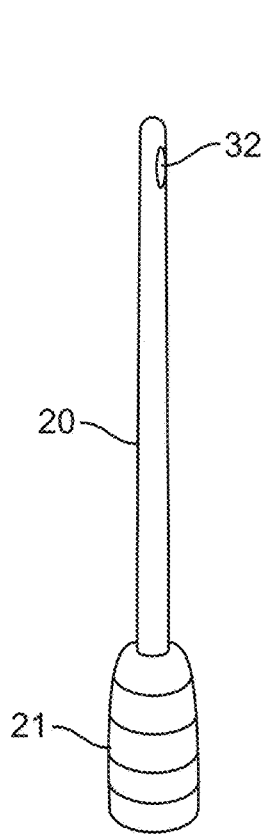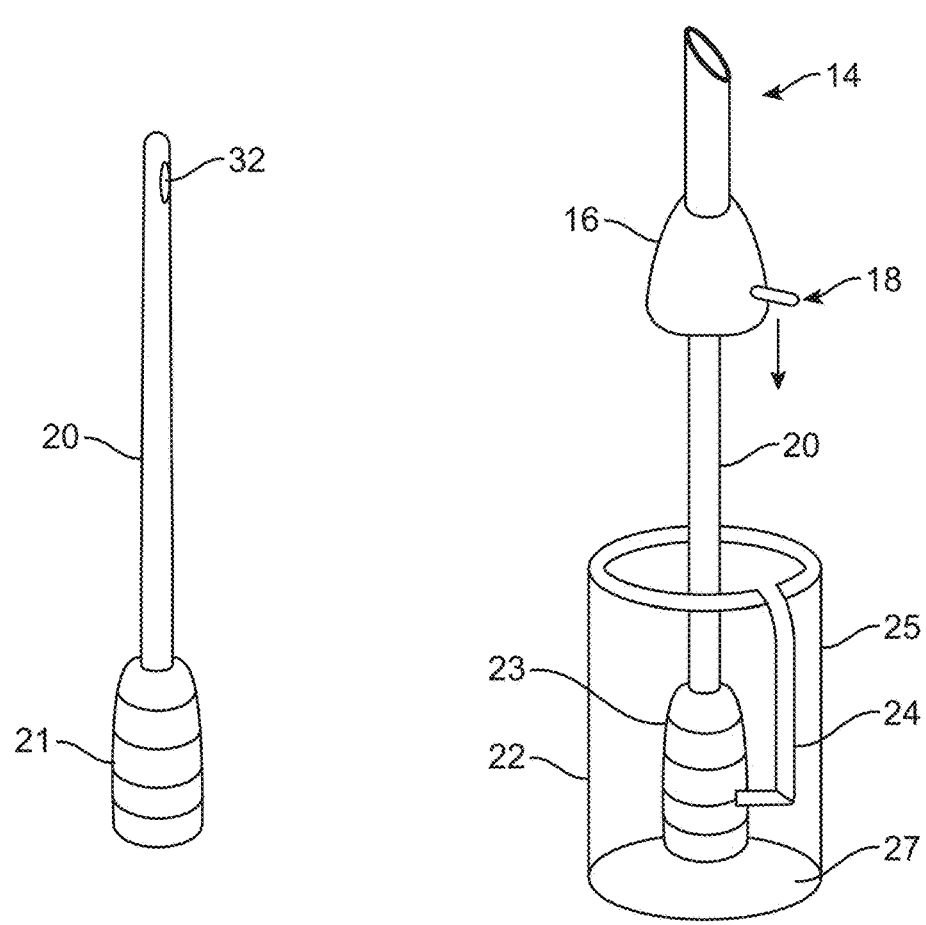
FIG. 2A          FIG. 2B
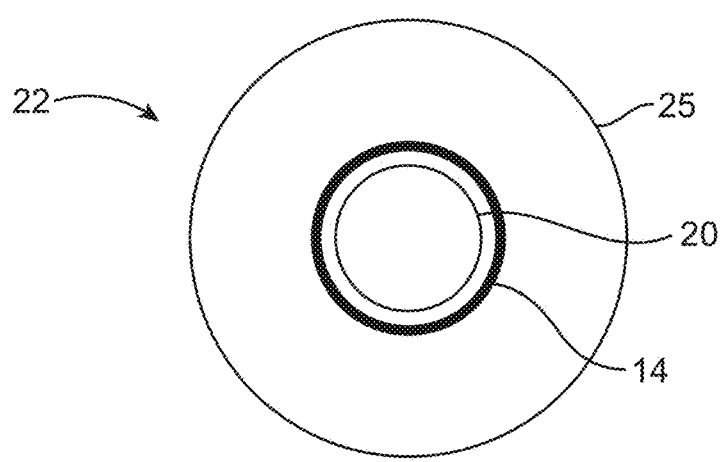
FIG. 2C

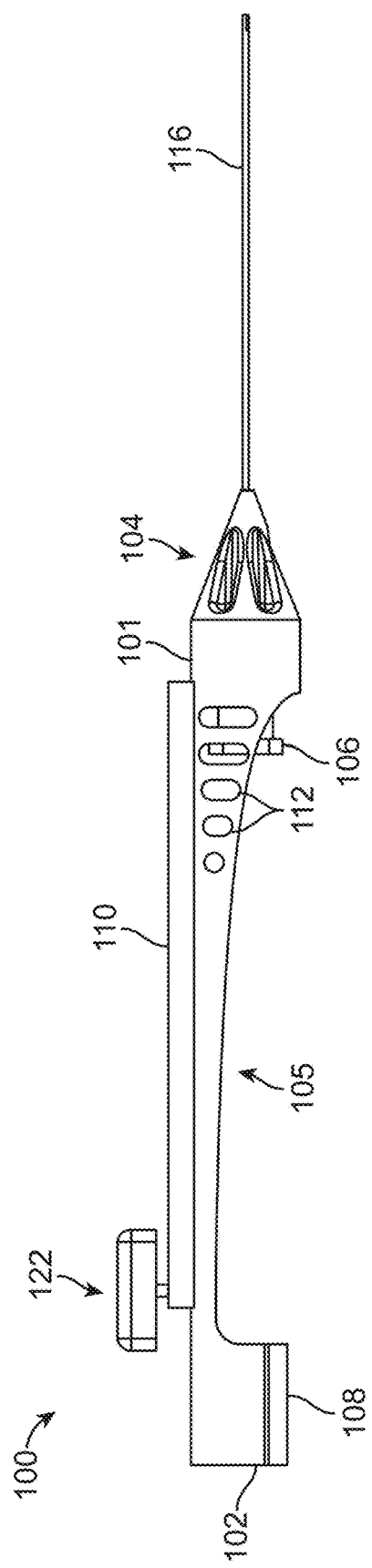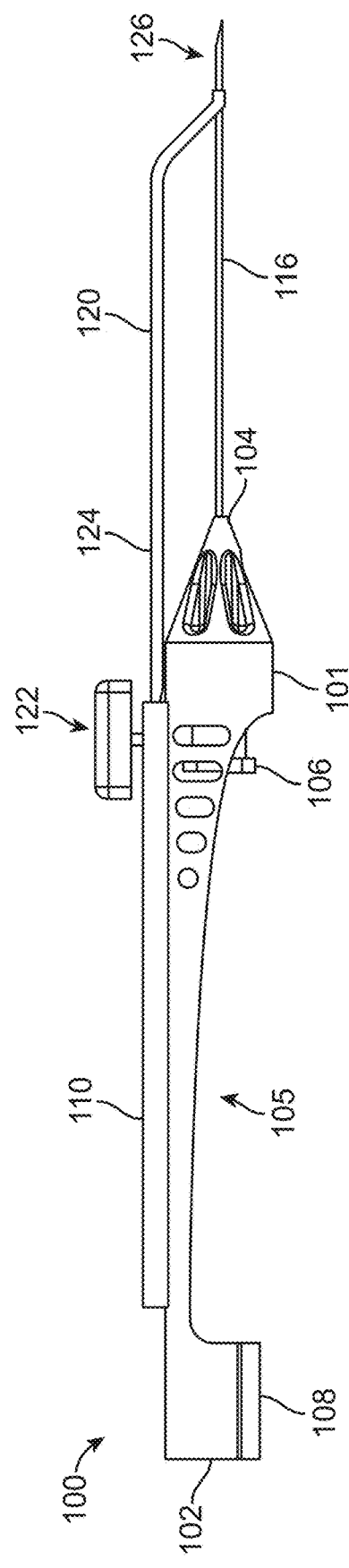
FIG. 8A
FIG. 8B

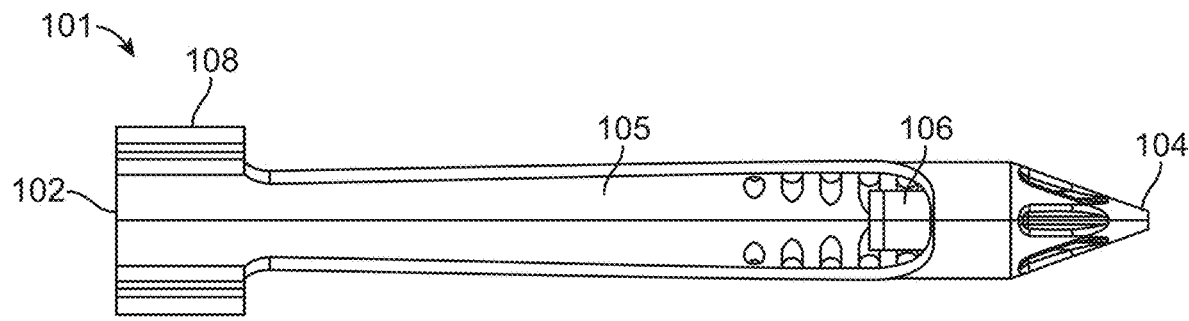
FIG. 9A
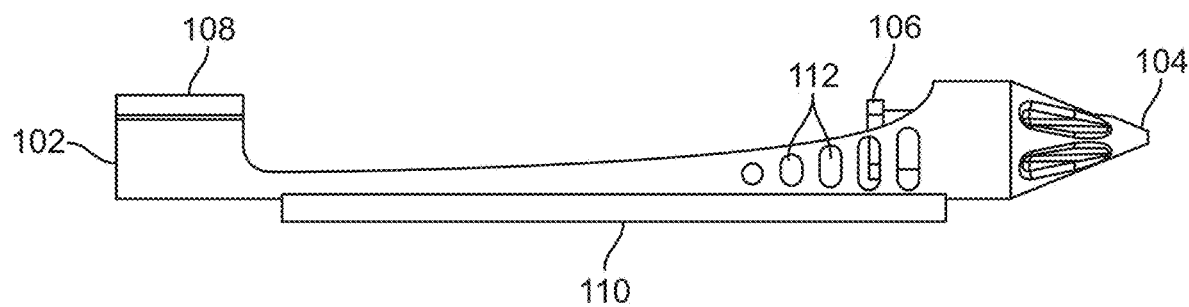
FIG. 9B
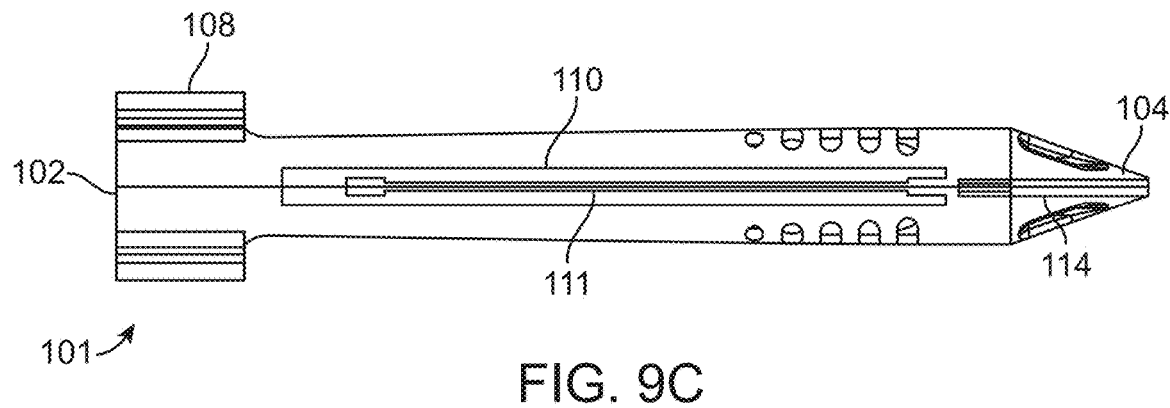
FIG. 9C
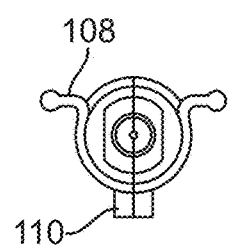
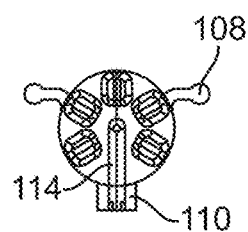
FIG. 9D    FIG. 9E

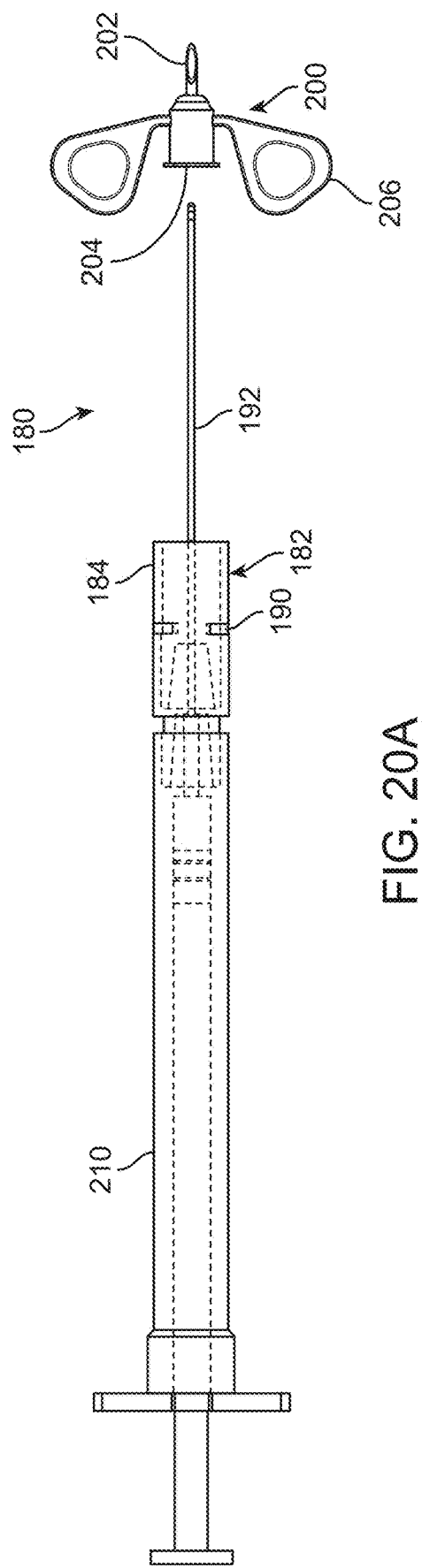
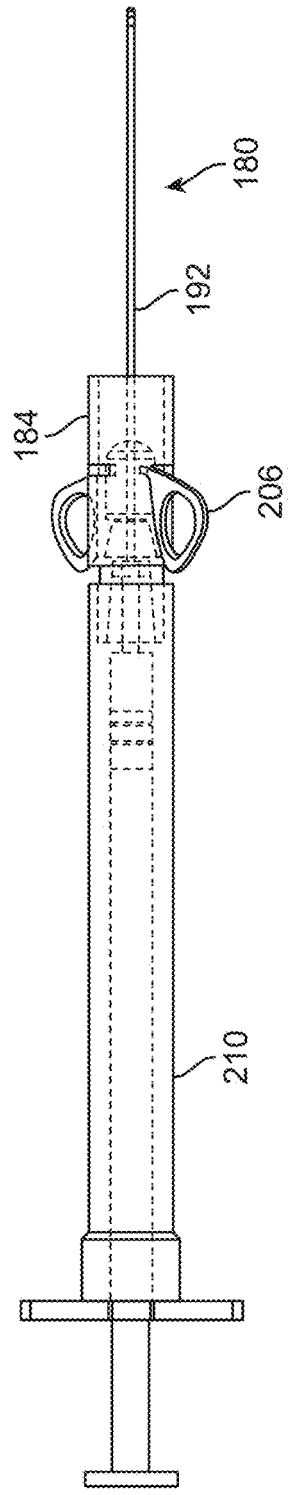
FIG. 20A
FIG. 20B

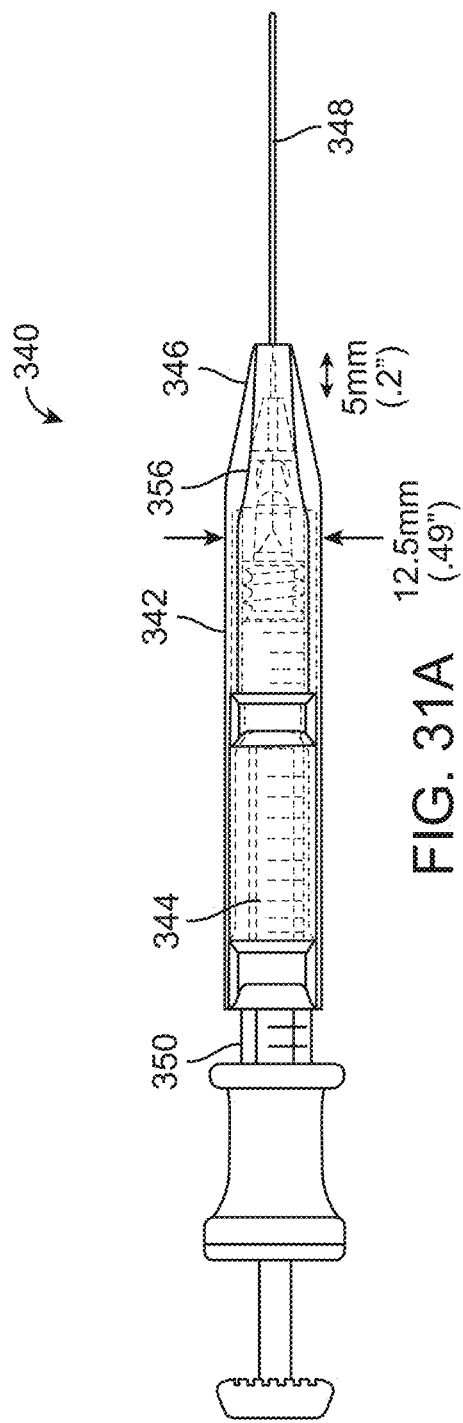
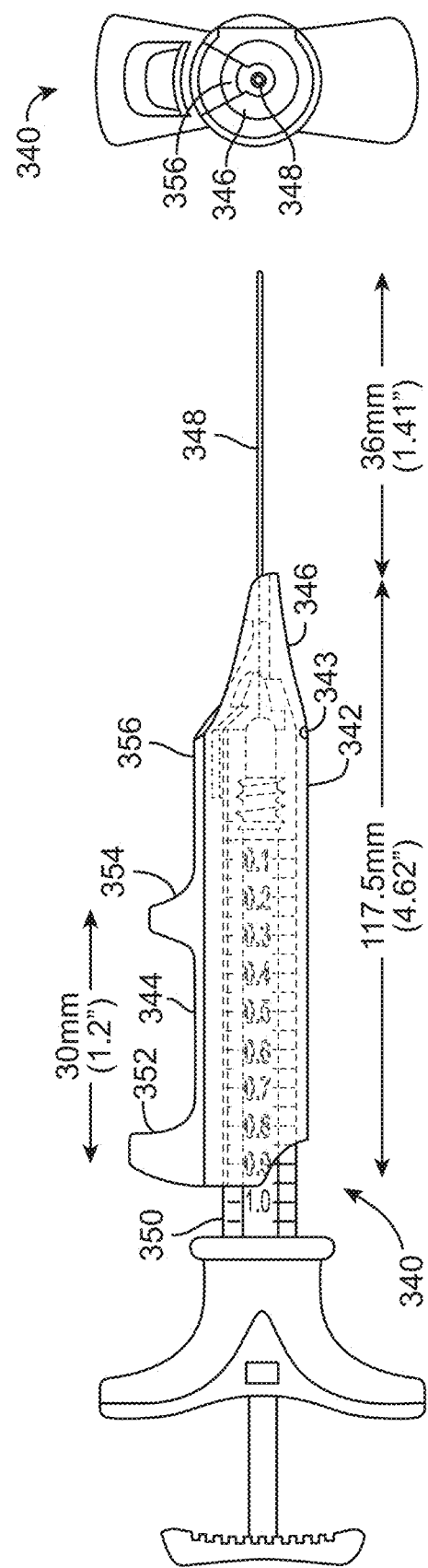
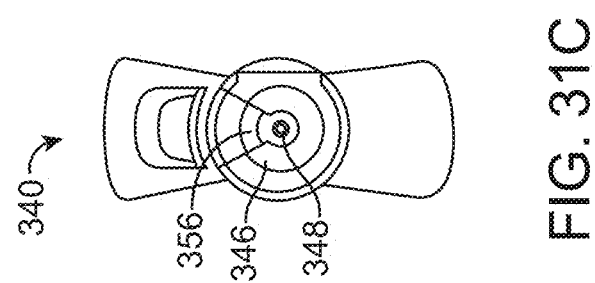
FIG. 31A
FIG. 31B
FIG. 31C

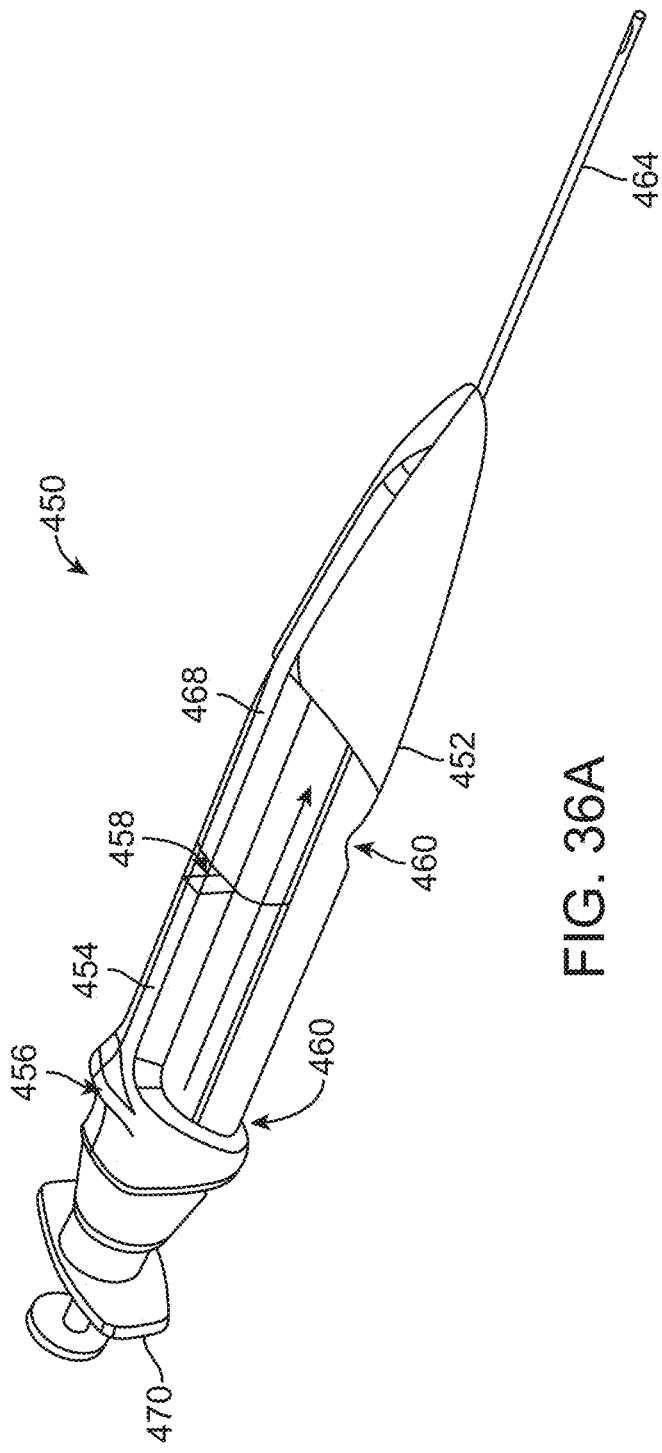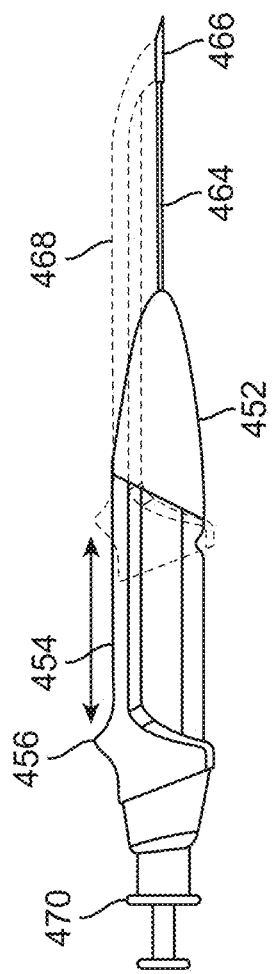
FIG. 36A
FIG. 36B

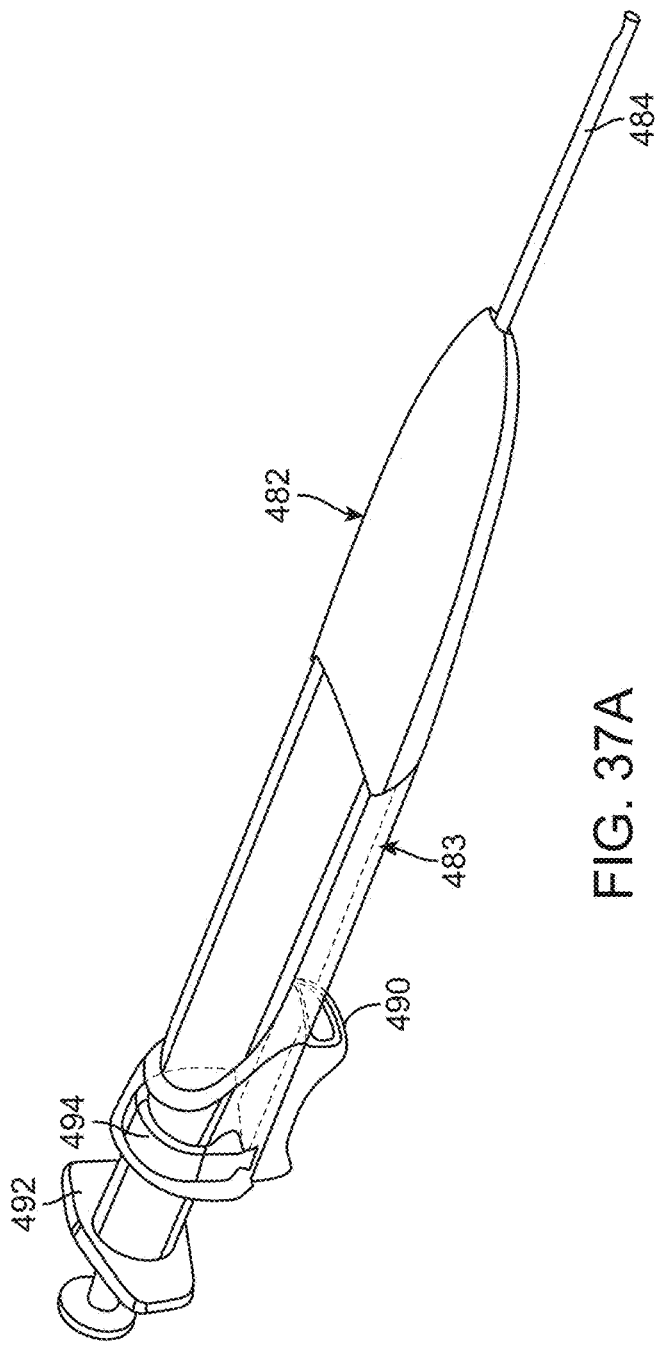
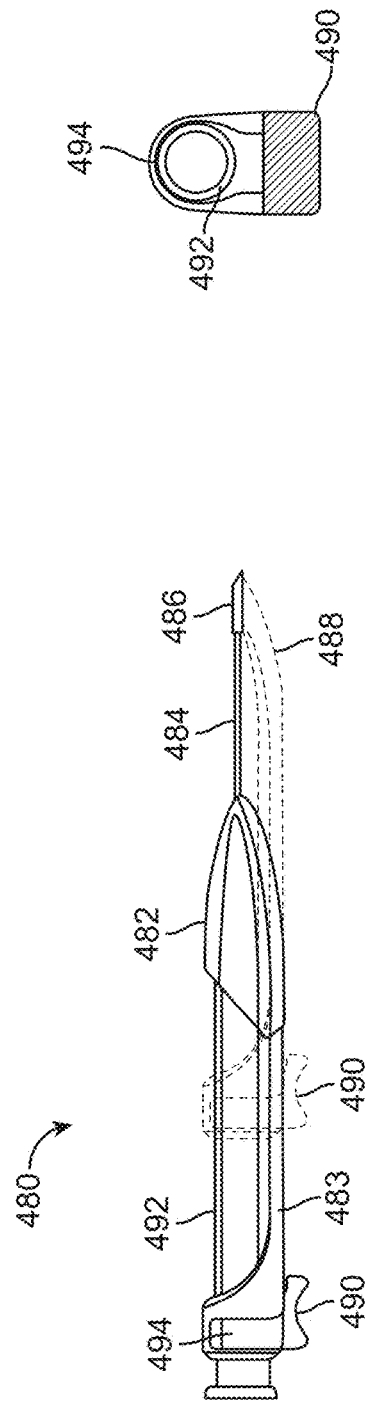
FIG. 37A
FIG. 37C
FIG. 37B

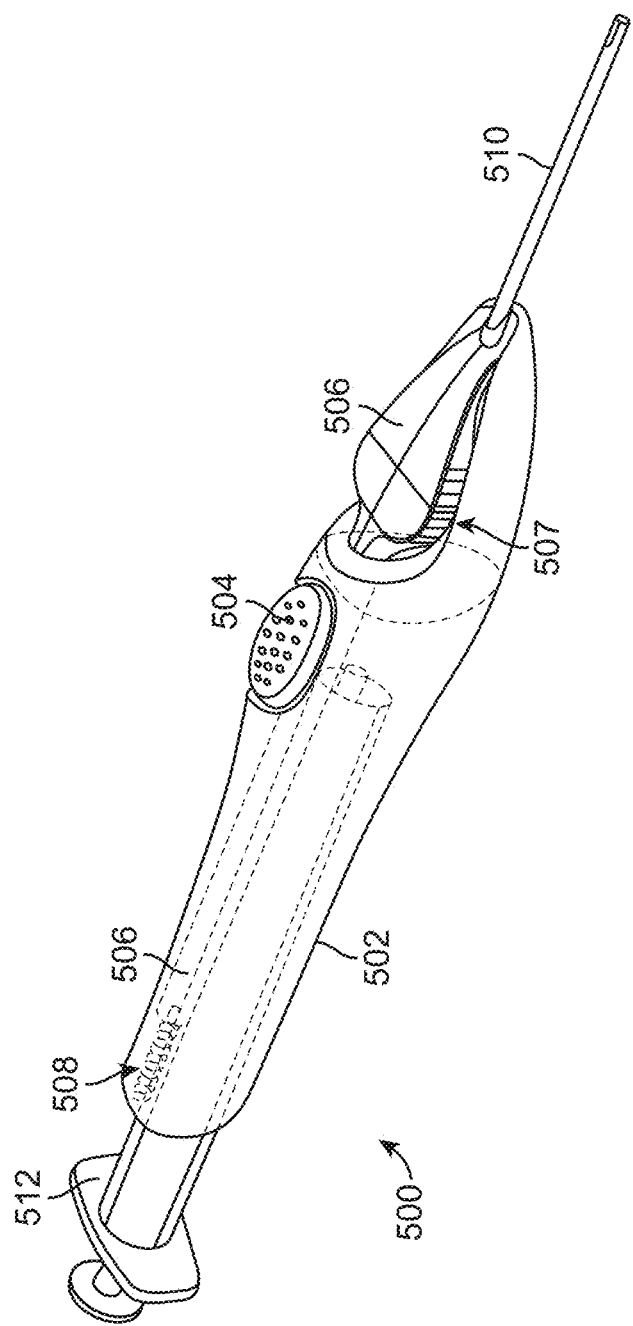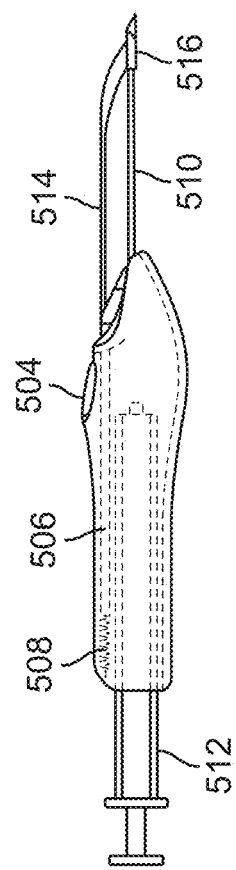
FIG. 38A
FIG. 38B

COMBINED NEEDLE AND CANNULA

CROSS-REFERENCE TO RELATED APPLICATIONS

This application claims the benefit of U.S. Provisional Patent Application No. 63/015,981, filed Apr. 27, 2020, entitled, "NEEDLE CANNULA" and U.S. Provisional Patent Application No. 63/092,855, filed Oct. 16, 2020, entitled, "COMBINED NEEDLE AND CANNULA". The disclosures of these priority applications are hereby incorporated by reference in their entirety into the present application.

TECHNICAL FIELD

The present application is related to medical devices and methods. More specifically, the application describes a combined needle and cannula device for injecting substances into or under the skin.

BACKGROUND

Medical practitioners, such as plastic surgeons, dermatologists, otolaryngologists ("ENT surgeons"), ophthalmologists, aestheticians and other healthcare providers, perform many different medical and surgical procedures on the face and other parts of the body to restore or improve the body's aesthetic appearance. One general type of procedure is the injection of substances into or just below the skin, to restore, augment or otherwise improve the appearance of tissue. Popular injections include fillers, Botulinum Toxin ("Botox"), fat transfer and subcutaneous threads. Common areas to inject substances into or below the skin are the face, neck, hands, breasts, and buttocks. These injections are typically performed in a medical clinic by physicians, physician assistants, trained aestheticians, or other healthcare providers trained in filler injections.

Dermal and sub-dermal (below the skin) injections are typically performed using a needle attached to a syringe. While a sharp-tipped needle is useful for penetrating a patient's skin, the needle can cause unwanted damage as the physician moves it below the skin or when it is used to inject the sub-dermal substance. This damage may include bruising, blood vessel laceration and bleeding, soft tissue necrosis (cell death) and even blindness and stroke, if injections are being performed around the eyes. Sharp needles may also lacerate nerves and blood vessels, and may puncture a vessel, resulting in injection of a filler directly into the vessel, causing embolization and tissue damage at the site. Due to these potential complications, many practitioners who perform injections now use an injection technique that involves first forming a puncture hole in the skin with a sharp hypodermic needle and then passing a blunt-tipped cannula through the puncture hole to the target area beneath the skin to inject the substance. Due to the added safety and reduced risk of complications, this two-step, needle-and-cannula technique is becoming a preferred method for dermal and sub-dermal filler injections.

The primary drawbacks with the two-step, needle-and-cannula method are: (1) it is cumbersome for the clinician to perform and thus often sub-optimal for both the clinician and the patient; and (2) it risks infection due to the use of a first device to puncture the skin and a second device passing through the puncture hole. First, the clinician pokes a hole through the epidermis and dermis with the sharp needle. Then, the clinician must remove the needle from the skin and set it aside, thus turning away from the patient and the tiny hole she just created, at least for a moment, to pick up the cannula. The clinician then must locate the hole on the surface of the skin, which can be challenging, and insert the blunt cannula tip through the hole. If the clinician cannot find the hole or cannot insert the cannula through the hole, she must create yet another hole with the needle and try again with the cannula. This can be cumbersome, time consuming and even embarrassing for the clinician, not to mention painful or at least uncomfortable for the patient. As stated above, the procedure may also pose safety concerns.

Many skin injection procedures require multiple entry points into the skin. Thus, this two-step procedure must be repeated multiple times on a typical patient. For example, a cheek augmentation sub-dermal injection may involve 2-3 injections sites for each cheek, thus requiring the clinician to repeat the cumbersome process 4-6 times for one patient. As a result, many medical practitioners are reluctant to adopt the current two-step, needle-and-cannula process and instead simply use a hypodermic needle attached to a syringe to administer sub-dermal substances. Although blunt-tipped cannula use for the administration of sub-dermal substances should be the standard of care for these procedures, the current technical and practical difficulties in using them in two un-integrated steps prevent further adoption of the safer cannula technique.

Other inventors have addressed at least some of the drawbacks described above. For example, U.S. Pat. Nos. 10,286,161 and 10,322,264 and U.S. Patent Pub. No. 2019/0275262 (a continuation of U.S. Pat. No. 10,286,161) address some of these issues. Each of the prior art devices, however, includes shortcomings in terms of device complexity, safety, ease of use, etc. Therefore, improvements to the devices and methods discussed in these references would be beneficial.

Therefore, it would be desirable to have an improved device and method for performing injections into and below the skin. Such a device and method should allow the clinician to easily and consistently form a puncture hole and advance a cannula to a target location in or under the skin. Ideally, this method would be performed without the clinician needing to turn away from the patient or relocate a puncture hole. Also ideally, the device would be easy and convenient for the clinician to use, even when multiple injection sites are required on a patient. This application addresses at least some of these objectives.

SUMMARY

An injection device described in this application generally includes a syringe holder, a cannula and a needle. The needle is used to pierce the skin and is then retracted to a safe position. The cannula can then be further advanced below the epidermis and in some cases below the dermis, to perform an injection at a target area. The needle has a sharp tip and the cannula has a blunt tip. A slider on the syringe holder is used to advance and retract the needle. When a substance has been injected at a first site, the device is removed from the patient and may optionally be prepared for a second injection site by removing the sharp point from the needle guard, repositioning it over the tip of the cannula and repeating the procedure.

The device can be a single unit, where the sharp point is attached to the cannula, and advanced and retracted as needed. For a two-component device, the sharp point can be a separate unit; used to pierce the skin, kept in place while the cannula is introduced through the skin, then retracted and covered while the injection of filler is completed. In some embodiments, a complete system, including a needle, a cannula, a needle guard and a syringe may be provided. In other embodiments, the system may include only a needle, a cannula and a needle guard. In an even simpler embodiment, only a cannula and a needle guard may be provided, and the needle may be "off the shelf." Or even the needle guard by itself may be provided for use with off the shelf cannula, needle and syringe.

In one aspect of the present disclosure, a device for performing injections in a patient includes a syringe holder comprising a needle guard, a cannula extending from the syringe holder and having a blunt tip and a cannula length, a needle slidably disposed over the cannula and having a sharp tip and a needle length that is shorter than the cannula length, and a slider on the syringe holder, coupled with the needle. The slider is configured to slide the needle along the cannula from an extended position, in which the sharp tip of the needle is located at or immediately adjacent the blunt tip of the cannula, to a retracted position, in which the sharp tip is housed within the needle guard of the syringe holder.

In some embodiments, the device may also include a support arm connecting the needle to the slider. In some embodiments, the device may include a track on the syringe holder, where the slider slides along the track, a distal locking feature on the track or the syringe holder for locking the slider in a distal location on the track, corresponding to the extended position of the needle, and a proximal locking feature on the track or the syringe holder for locking the slider in a proximal location on the track, corresponding to the retracted position of the needle. Optionally, the device may also include a release mechanism on the slider for unlocking the slider from the distal locking feature or the proximal locking feature to allow the slider to slide along the track. For example, the release mechanism may be a button. In some embodiments, the slider includes a proximal finger stop feature and a distal finger stop feature.

The syringe holder may include a Luer lock for coupling with a syringe to place a barrel of the syringe in fluid communication with the cannula. In some embodiments, at least part of the syringe holder is transparent, so a user of the device can read markings on a syringe through the syringe holder. In some embodiments, the syringe holder comprises a cylinder into which a syringe is inserted for use. Alternatively, the syringe holder may include an open side into which the syringe is inserted for use. The needle guard may be a housing on a distal end of the syringe holder. Optionally, the device may also include a cannula hub attached to a proximal end of the cannula and housed within the housing. In some embodiments, the housing has a conical shape.

In various embodiments, the slider is configured to slide a distance of between about 40 mm and about 50 mm from the extended position to the retracted position. In various embodiments, the syringe holder has a length of between about 115 millimeters and about 120 millimeters. The cannula length is between about 30 millimeters and about 45 millimeters in various embodiments. Optionally, the device may further include an automatic needle retraction mechanism coupled with the syringe holder and the slider, to automatically retract the needle into the needle guard.

In another aspect of the invention, a method of performing an injection on a patient may involve attaching a syringe to a syringe holder of an injection device and inserting a sharp tip of a needle of the injection device together with a blunt tip of a cannula of the injection device through an epidermis and at least partially through a dermis of the patient. The needle is mounted on the cannula. Next, the method involves retracting the needle over the cannula, while maintaining the tip of the cannula in position under the skin, to remove the sharp needle tip from the patient and position the sharp tip within a needle guard of the injection device. Next, the user advances the cannula to a target location in or below the dermis. Once at the cannula is advanced to a desired location, the method involves injecting a substance from the syringe through the cannula to the target location and removing the cannula from the patient.

In some embodiments, the method may involve, after attaching the syringe, advancing the needle over the cannula to an extended position, in which the sharp tip of the needle is located at or immediately adjacent the blunt tip of the cannula. In some embodiments, the method may further involve, after removing the cannula from the patient: advancing the needle over the cannula again to place the needle in the extended position; inserting the sharp tip of the needle and the blunt tip of the cannula through the epidermis and at least partially through the dermis in a different location on the patient; retracting the needle over the cannula to remove the sharp tip from the patient and position the sharp tip within a needle guard of the injection device; advancing the cannula to a new target location in or below the dermis; injecting a substance from the syringe through the cannula to the new target location; and removing the cannula from the patient.

In some embodiments, the method further involves locking the needle inside the needle guard after retracting the needle and before injecting the substance. The method may optionally further involve locking the needle in an extended position where the sharp tip is located at or immediately adjacent the blunt tip of the cannula before inserting the sharp tip of the needle through the epidermis. The method may further involve unlocking the needle from the extended position before retracting the needle.

In some embodiments, attaching the syringe to the syringe holder involves attaching the syringe to a Luer lock feature of the syringe holder. In some embodiments, retracting the needle involves triggering an automatic retraction mechanism of the syringe holder. In some embodiments, retracting the needle involves sliding a slider proximally along the syringe holder, where the slider is coupled with the needle. In some embodiments, sliding the slider involves sliding the slider a first distance along the syringe holder using a first finger stop feature on the slider and sliding the slider a second distance along the syringe holder using a second finger stop feature on the slider.

In some embodiments, injecting the substance comprises depressing a plunger of the syringe. Depressing the plunger may involve holding two finger hold features of the syringe holder with two fingers of a hand while depressing the plunger with a thumb of the hand. In some embodiments, the sharp tip of the needle and the blunt tip of the cannula are advanced through the dermis, and the target location is below the dermis. In some embodiments, the method may further include viewing a fluid level marking on the syringe through a transparent portion of the syringe holder. Any suitable substance may be injected, such as but not limited to hyaluronic acid, calcium hydroxylapatite, poly-L-lactic acid, polymethylmethacrylate, autologous fat, other dermal fillers, collagen, collagen production stimulators or nerve toxins.

In another aspect of the present disclosure, a device for performing injections in a patient may include: a needle having a sharp tip and an inner diameter; a cannula having a blunt tip, a cannula hub for connecting with a syringe, a length that is longer than that of the needle, and an outer diameter that is smaller than the inner diameter of the needle; and a needle guard for shielding the needle when it is retracted. In some embodiments, the needle further includes a needle hub that fits over the cannula hub when the needle is fully retracted and a locking feature on the cannula hub for locking the needle within the needle guard.

The needle guard may include a mating locking feature for coupling with the locking feature of the cannula hub. The locking feature may include a protrusion on the hub of the needle, and the mating locking feature may be a slot, a locking tab or a pressure fit member into which the protrusion fits. In some embodiments, the cannula hub is configured to attach to the syringe via a Luer lock mechanism. In some embodiments, an outer surface of the needle guard is made of a flexible material such as but not limited to plastic, rubber or a polymer. In some embodiments, at least part of the needle guard is a cylindrical wall, and an inner diameter of the cylindrical wall is greater than an outer diameter of a hub of the needle.

These and other aspects and embodiments are described in greater detail below, in relation to the attached drawing figures.

BRIEF DESCRIPTION OF THE DRAWINGS

FIG. 2A is a side perspective view of the cannula of FIG. 1;

FIG. 2B is a side perspective view of the cannula, needle, and needle guard of FIG. 1, with the needle in the forward/advanced position on the cannula;

FIG. 2C is a top, cross-sectional view of the needle guard, needle, and cannula of FIG. 1;

FIGS. 8A and 8B are side views of a needle cannula system for performing injections, with the needle retracted (FIG. 8A) and the needle advanced (FIG. 8B), according to another alternative embodiment;

FIGS. 9A-9E are bottom, side, top, rear and front views, respectively, of the syringe holding portion of the needle cannula system of FIGS. 8A and 8B;

FIGS. 20A and 20B are side views of the needle cannula system of FIGS. 17A-19B coupled with a syringe, with the needle portion separate from the cannula and hub portion (FIG. 20A) and the needle portion housed within the cannula and hub portion (FIG. 20B);

FIGS. 31A-31C are top, side and front views, respectively, of a needle and cannula device with a loaded syringe, according to one embodiment;

FIGS. 36A and 36B are perspective and side views, respectively, of a needle and cannula device for performing injections, according to another alternative embodiment;

FIGS. 37A-37C are perspective, side and end-on/cross-sectional views, respectively, of a needle and cannula device for performing injections, according to another alternative embodiment;

FIGS. 38A and 38B are perspective and side views, respectively, of a needle and cannula device for performing injections, according to another alternative embodiment;

DETAILED DESCRIPTION

Figure 1:
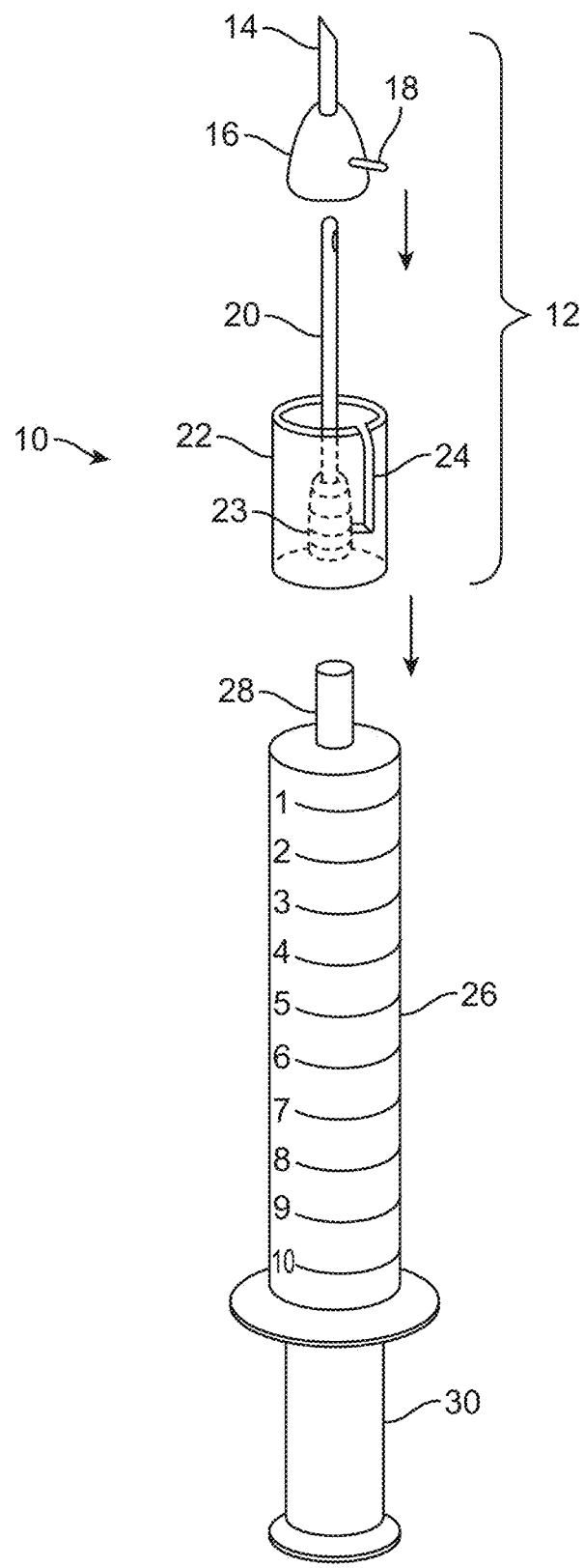
FIG. 1 a side view of a needle cannula system for performing injections, according to one embodiment.

The methods and devices described herein may be used for any injections on any part of the body, such as but not limited to the face, neck, breasts, buttocks and hands. In many instances, the methods and devices of this application are described for use in injecting substances such as dermal fillers into or below the dermis of the skin. The following description, therefore, often refers to "sub-dermal injections." The methods are not limited, however, to use for sub-dermal injections, and in various embodiments injections may be directed into dermis, sub-dermis, subcutaneous tissue, superficial fat, deep fat, pre-periosteum, or sub-periosteum, for example. To simplify this disclosure, this list of possible injection target tissues will not be repeated throughout, and the terms "sub-dermal injections" or "skin injections" may be used broadly. Any of the described embodiments, however, may be used to inject any suitable area or tissue.

Similarly, the methods and devices described herein may be used to inject any suitable substance. Although they are perhaps most suitable for injecting substances like fillers, such as hyaluronic acid, rather than Botox, which is usually injected with a short, small-gauge needle, the devices and methods may be used to inject any suitable substance. Examples of injectable substances that may be used with the devices and methods described herein include but are not limited to deoxycholic (bile) acid, hyaluronic acid (fillers), collagen-stimulating tumescent and autologous fillers (fat, platelet rich plasma), Botox and other brands of botulinum toxin, lidocaine, saline, synthetic wrinkle fillers (e.g., calcium hydroxyapatite, poly-1-lactic acid, polyglycolic acid), collagen wrinkle fillers, polymethylmethacrylate with bovine collagen, autologous wrinkle fillers, absorbable threads, non-absorbable threads and tumescent anesthesia solutions. Hyaluronic fillers are cross-linked hyaluronic acids, typically used to naturally augment the lips and fill areas of the face that lose volume with age, such as the temples, mid-cheek break, tear through, nasolabial fold and marionette lines. Collagen-stimulating fillers, such as Sculptra® poly-1-lactic acid, Radiesse® and calcium hydroxyapatite, are typically injected throughout the whole face to provide more structural volumizing. Any of these substances or combinations of substances may be injected, using the devices and methods described further below.

The needle and cannula device and method embodiments described below will ideally provide certain advantages over currently available devices and methods. For example, the needle cannula device should be easy to use and not require the physician or aesthetician to turn away from the patient, relocate the hole formed in the skin, etc. The device must also be safe for both the patient and the user, which means the needle portion of the device should likely be removed from the patient's skin while the cannula is being used for the injection. Additionally, the needle should be shielded when not in use, to protect the patient's skin and the user's fingers from harm. Ideally, the device will be ergonomically designed for ease of use, so that much or all of an injection might be performed with one hand. Portions of the method that cannot be performed with one hand should at least be simple to perform with two hands. It would also be ideal to have a structurally simple device that is inexpensive to manufacture, to avoid adding significant additional expense to an injection procedure. Finally, the device should be relatively simple to use multiple times on one patient, for example for performing two or more injections on a patient's face, in some instances as many as four or six or more injections. After the first injection, it would be ideal to have a device that was easy to prepare for a second injection, a third injection, etc. It would also be ideal for a user to be able to easily visualize at least part of the injection syringe during the injection procedure, to be able to easily assess and monitor how much substance remains in the syringe and thus how much substance has been injected. The devices and methods described in this application address at least some of these objectives.

Referring to FIG. 1, a side view of a combined needle and cannula injection system 10 is illustrated. In this embodiment, the system 10 includes a needle cannula device 12 and a syringe 26. As mentioned above, in various embodiments, the needle cannula device 12 may be provided by itself, for use with any suitable off the shelf syringe 26. In alternative embodiments, the complete system 10 may be provided, with either an off the shelf or custom syringe 26. This application includes any and all combinations of device and system components within its scope.

In the pictured embodiment, the needle cannula device 12 includes a needle 14, a cannula 20 and a needle guard 22. The needle 14 has a needle hub 16 and a protrusion 18 (or "handle"). The cannula 20 has a cannula hub, which is pictured in subsequent figures but is located within the needle guard 22 in FIG. 1. The needle guard 22 includes a guard hub 23 and a locking slot 24 for accepting the protrusion 18 and locking it in place to lock the needle 14 within the needle guard 22. The syringe 26 includes a distal tip 28 and a plunger 30. When assembled, the needle 14 fits over and slides along the cannula 20. The needle 14 slides proximally along the cannula 20 until the needle hub 16 fits over the guard hub 23. The inner diameter of the needle 14 and the needle hub 16, therefore, are large enough to fit over the outer diameter of the cannula 20 and the guard hub 23, respectively. In various embodiments, the cannula 20 may have a length of between about 30 mm and about 50 mm, and in one embodiment about 40 mm. The cannula may be 22, 25 or 27 gauge in diameter, for example. The protrusion 18 on the needle hub 16 is used by the physician to slide the needle down the straight portion and then perpendicularly into the lock portion of the locking slot 24 to lock the needle 14 within the needle guard 22.

The guard hub 23 fits over the cannula hub (see FIG. 2A), which in turn fits over the distal tip 28 of the syringe 26. In some embodiments, the syringe distal tip 28 may be a Luer lock that the cannula hub is configured to mate with. In other embodiments, the cannula hub may fit onto the distal tip by pressure fit, screw threads, snap fit or any other suitable attachment mechanism. The outer diameter of the needle guard 22 may be the same as, less than or greater than an outer diameter of the barrel of the syringe 26.

FIG. 2A shows the cannula 20 in further detail, including the cannula hub 21 and a distal injection port 32, through which substances are injected into the patient. The shape and size of the cannula hub 21 are designed to allow it to fit over the distal tip 28 of the syringe 26 and within the guard hub 23 of the needle guard 22.

FIG. 2B shows the cannula 20, needle guard 22 and needle 14, with the needle 14 in its forward/advanced position at the tip of the cannula 20. FIG. 2B also shows additional detail of the needle guard, which includes a cylindrical sidewall 25 with the locking slot 24, as well as a platform 27 connecting the sidewall 25 to the guide hub 23. In some embodiments, the platform 27 fits down on a corresponding distal surface of the syringe 26. In some embodiments, the cannula 20 and the needle guard 22 are manufactured to be one piece. Alternatively, the cannula 20 and needle guard 22 may be two separate pieces and may even be separated by a user, for example if a new cannula 20 is desired to be used with the same needle guard 22. As shown in FIG. 2B, the needle 14 fits down over the cannula 20. It may be used to puncture the skin and then is slid proximally over the cannula 20 (solid-tipped arrow) so that the protrusion 18 slides through the locking slot 24 in the sidewall and then turned to the side to lock the needle 14 in the needle guard 22. The needle guard 22 is long enough to shield the sharp tip of the needle 14 from exposure to the patient and the user of the device 12. In some embodiments, the sidewall 25 of the needle guard 22 may be made of a relatively rigid material, such as but not limited to metal or plastic. Alternatively, in some embodiments the sideway 25 and/or other parts of the needle guard 22 may be made of a flexible or elastic material, such as but not limited to rubber or any suitable polymer. In such embodiments, the sidewall 25 may be able to stretch to fit around the needle hub 16 and then may trap the needle hub 16 in place within the needle guard 22. This mechanism may be used in place of or in addition to the locking slot 24, for example.

Figure 2D:
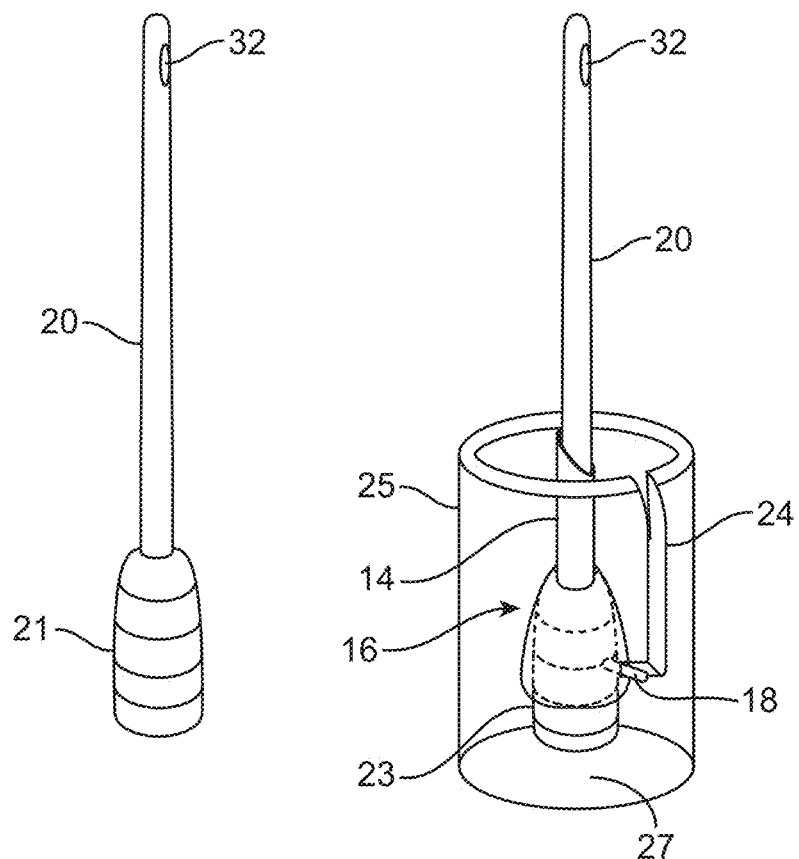
FIG. 2D is a side perspective view of the needle, cannula, and needle guard with the needle in the retracted position on the cannula, within the needle guard.

FIG. 2C is a top, cross-sectional view of the needle guard 22, the needle 14 and the cannula 20. This figure illustrates how the three parts fit together. FIG. 2D is a side perspective view, showing the needle 14 retracted proximally over the cannula 20 and within the needle guard 22. In this configuration, the cannula 20 can be further positioned within the sub-dermal space if desired, and the substance can be injected into the patient through the cannula 20.

Figure 3A:
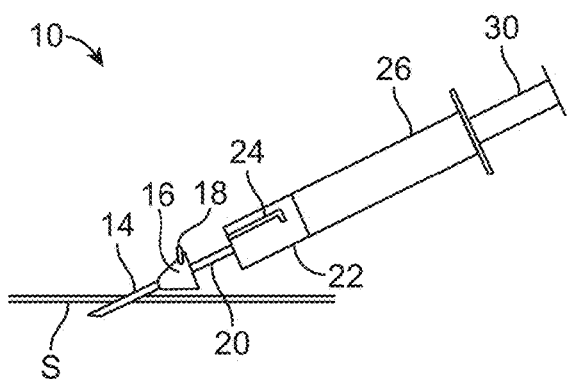
FIGS. 3A-3D are side views of a needle cannula device illustrating a method for performing a sub-dermal injection, according to one embodiment.
Figure 3B:
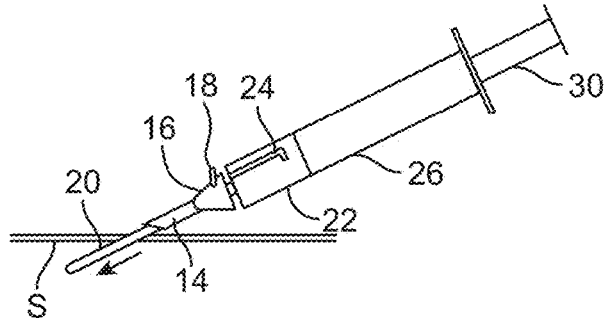
Figure 3C:
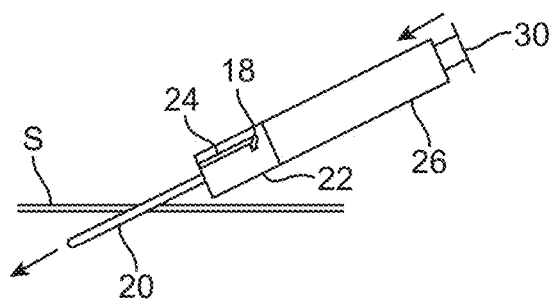
Figure 3D:
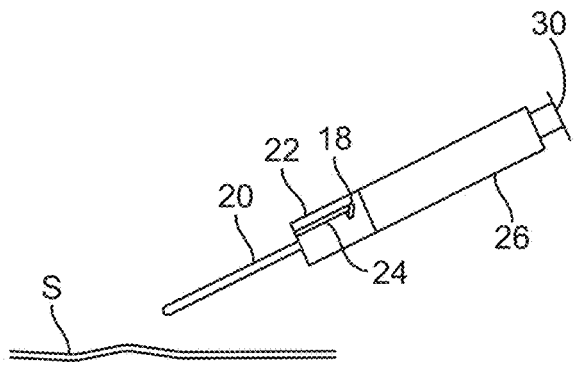

Referring now to FIGS. 3A-3C, a method for performing a sub-dermal injection using the needle cannula system 10 is illustrated. In FIG. 3A, needle 14 is in its advanced (or "forward") position, relative to the cannula 20, and the needle 14 has been used to puncture through the epidermis and dermis of the skin S. In FIG. 3B, the user is now advancing the distal end of the cannula 20 through the needle 14 and below the skin S. Next, as illustrated in FIG. 3C, the needle 14 is retracted back (proximally) into the needle guard 22, and the protrusion 18 is locked in place within the locking slot 24, to prevent it from moving. At this point, the cannula 20 may be further manipulated sub-dermally, if desired, and then the substance is injected (hollow-tipped arrow) by depressing the plunger 30 of the syringe 26. When the injection is complete, the cannula 20 is removed from the skin S, as in FIG. 3D, in this case leaving a slightly rounded, augmented area of skin S.

To repeat the above-described method on another area of the patient's skin, the needle 14 can be simply unlocked from the locking slot 24 and advanced to its advanced position on the cannula 20 to be ready to form another skin puncture and repeat the injection process. In various embodiments, the method may be performed only once or as many times as suitable for a given patient. In some embodiments, the syringe 26 may be swapped out after one or more injections, to provide additional substance. Similarly, the cannula 20 and/or the needle 14 may also be replaced during a multiple-injection treatment on the same patient, for example if a sharper needle 14 is desired. In other embodiments, all parts of the system 10 may be provided as one unit that is used for one patient and then disposed of all together.

Figure 4:
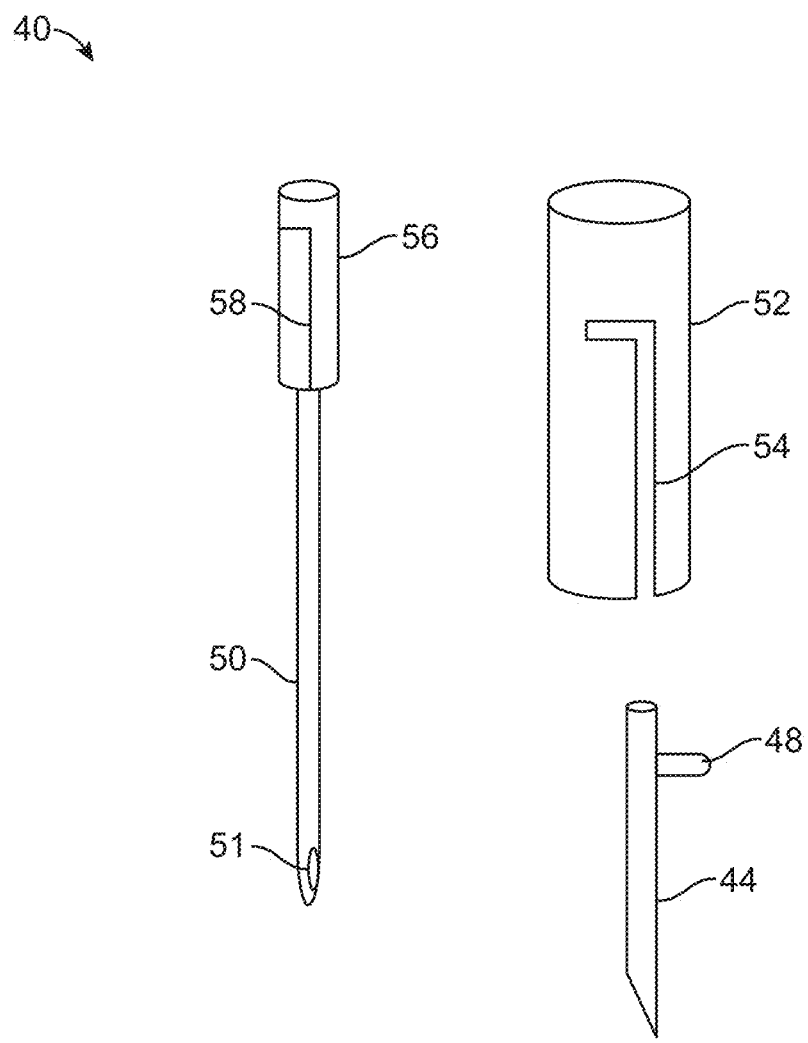
FIG. 4 an exploded perspective view of a needle cannula system for performing injections, according to an alternative embodiment.

Referring now to FIG. 4, an alternative embodiment of a combined needle and cannula device 40 is illustrated. In this embodiment, the needle cannula device 40 includes a needle 44 with a protrusion 48 (or "arm" or "handle"), a needle guard 52 with a locking slot 54, and a cannula 50 with an injection port 51, a hub 56 and a cannula slot 58, which corresponds to the locking slot 54. This needle cannula device 40 functions much the same as the one described previously, although the needle 44 does not include a hub.

Figure 5A:
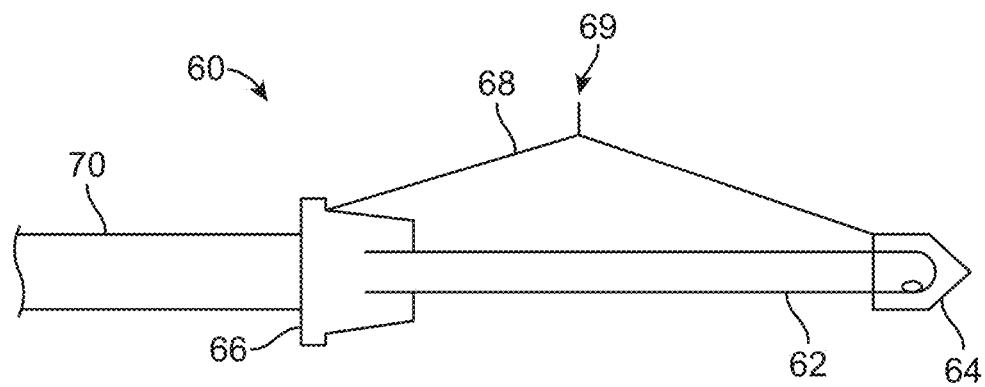
FIGS. 5A and 5B are side views of a needle cannula system for performing injections, according to another alternative embodiment.
Figure 5B:
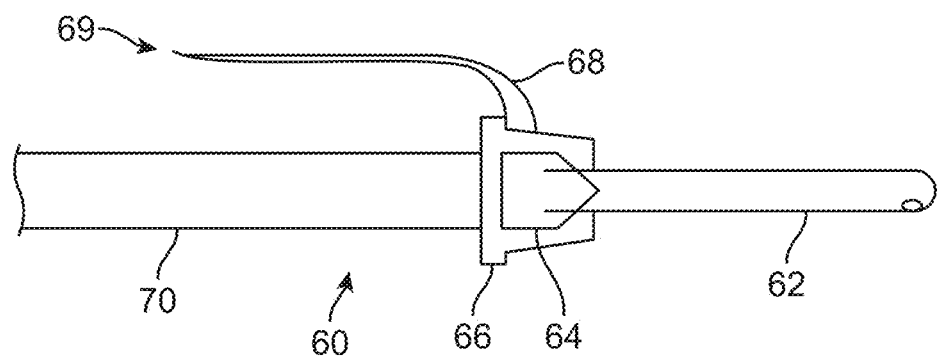

FIGS. 5A and 5B illustrate another alternative embodiment of a combined needle and cannula device 60. This embodiment includes a syringe 70, a needle tip 64, a cannula 62, a needle guard 66 and a connector 68 with a hinge 69. The connector 68 attaches the needle tip 64 to the needle guard 66, thus ensuring that the needle tip 64 does not fall off the distal end of the cannula 62 and providing a mechanism for retracting the needle tip 64. FIG. 5A shows the needle tip 64 in its advanced position for puncturing the skin. FIG. 5B shows the needle tip 64 retracted proximally along the cannula 62 and within the needle guard 66 and the connector pulled back. The needle guard 66 may hold the needle tip 64 with any suitable mechanism, such as but not limited to pressure fit, tabs, snap fit, threads or the like. To ready the needle cannula device 60 for a second injection, the connector 68 may be pulled and/or the needle guard 66 may be squeezed to eject the needle tip 64 from the guard 66.

Figure 6:
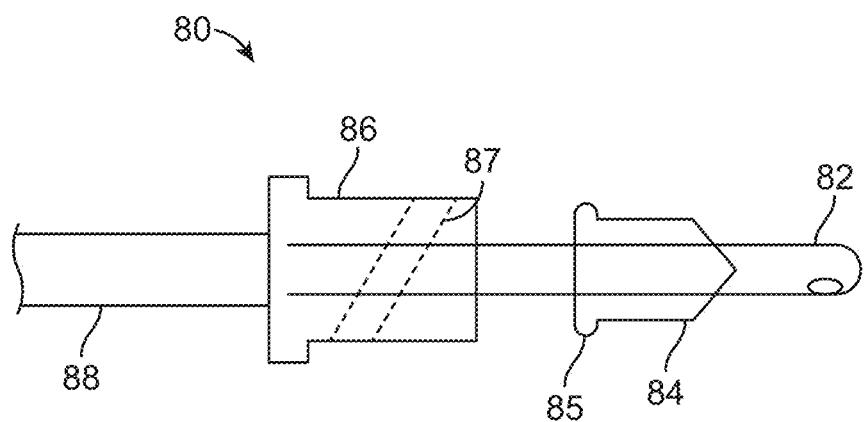
FIG. 6 is a side view of a needle cannula system for performing injections, according to another alternative embodiment.

FIG. 6 illustrates another alternative embodiment of a combined needle and cannula device 80, including a syringe 88, a cannula 82, a needle tip 84 and a needle guard 86. In this embodiment, the needle tip 84 includes a proximal tab 85, which fits within a slot 87 on the needle guard 86, to hold the needle tip 84 in the guard 86.

Figure 7:
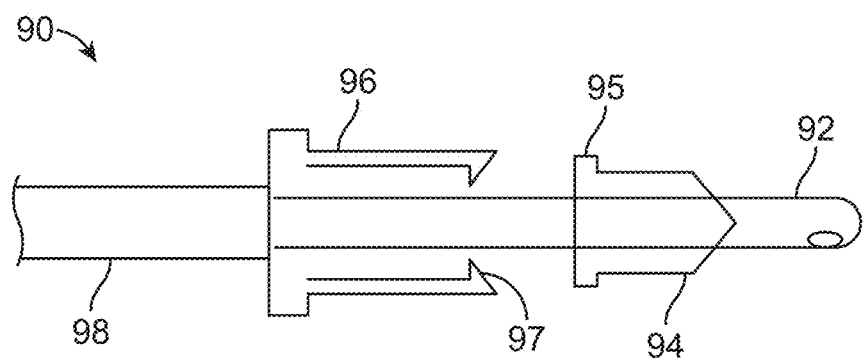
FIG. 7 is a side view of a needle cannula system for performing injections, according to another alternative embodiment.

FIG. 7 illustrates another alternative embodiment of a combined needle and cannula device 90, including a syringe 98, a cannula 92, a needle tip 94 and a needle guard 96. In this embodiment, the needle tip 94 includes a proximal tab 95, which fits within a locking tab 97 on an inner surface of the needle guard 96, to hold the needle tip 94 in the guard 96. To release the needle tip 94 from the guard 96, the user simply squeezes the guard 96 at or near its proximal end, to widen the end with the locking tabs 97 and thus allow the needle tip 94 to advance distally along the cannula 92.

Referring now to FIGS. 8A-13, another embodiment of needle cannula system 100 for penetrating through the epidermis of the skin (and in some cases the dermis) and injecting a filler or other substance is illustrated. The complete system 100 is illustrated by itself in FIGS. 8A-8B and with an attached syringe 130 in FIGS. 12 and 13. A syringe holder 101 (or "syringe cradle") portion of the system 100 is illustrated by itself in FIGS. 9A-9E, 10A and 10B. A needle holder 120 portion of the system 100 is illustrated by itself in FIG. 11. Referring to FIGS. 8A and 8B, in this embodiment the needle cannula system 100 includes the syringe holder 101 and the needle holder 120. The syringe holder 101 includes a proximal end 102, a distal end 104, a concave syringe channel 105, a proximal syringe clamp 108, a female luer connector 106 for connecting with a syringe, a slider track 110, side windows 112 to allow the user to see how much fluid remains in the end of the syringe barrel, and a cannula 116 extending from the distal end 104. The needle holder 120 includes a thumb slider 122 attached to a support arm 124, which is in turn attached to a needle 126, which rides over the cannula 116. FIG. 8A shows the needle cannula system 100 with the needle holder 120 fully retracted proximally and the needle 126 housed within the syringe holder 101. FIG. 8B shows the needle cannula system 100 with the needle holder 120 fully advanced, so the needle 126 is in a position to puncture through the epidermis. The needle holder 120 is advanced and retracted via the thumb slider 122. The features and operation of the needle cannula system 100 are described in further detail below.

FIGS. 9A-9E are bottom, side, top, rear and front views, respectively, of the syringe holder 101 of the needle cannula system 100. The top view of FIG. 9C shows that the slider track 110 includes a slot 111, through which the needle holder 120 slides. The top view also shows a needle housing 114 on the syringe holder 101, where the needle 126 resides when the needle holder 120 is retracted. When retracted as such, the needle 126 is out of the way and thus cannot harm the physician user or the patient.

The bottom view of FIG. 9A shows the syringe channel 105, wherein the syringe 130 (not shown in this figure) rests when in use. The syringe clamp 108 is built to have at least some give and resiliency, so that it can stretch to accommodate a syringe barrel and then snap back to its default shape and size to hold the syringe barrel in place. The entire syringe holder 101 may be made of one material or of multiple materials attached together. For example, the syringe holder 101 may be made of any suitable plastic, polymer or metal. Typically, although not necessarily, the syringe holder 101 is disposable, so it may be made of a material (or combination of materials) that is inexpensive enough to make the device readily disposable.

Figure 10A:
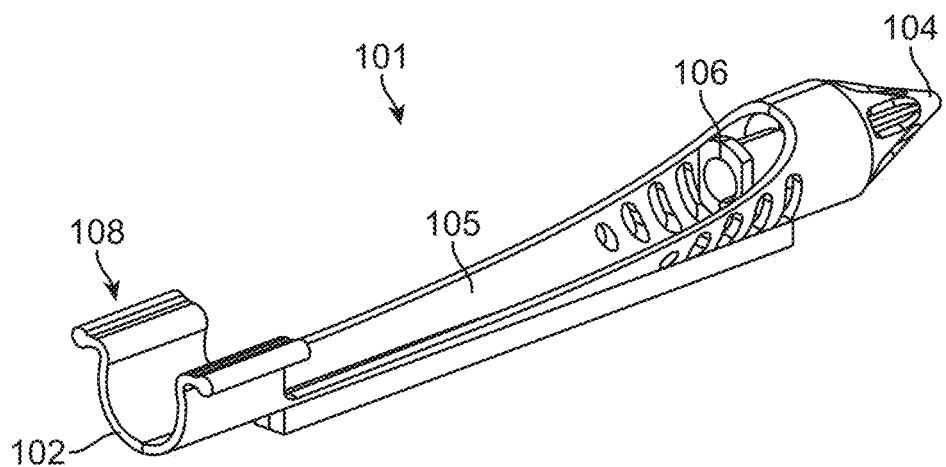
FIGS. 10A and 10B are bottom perspective and top perspective views, respectively, of the syringe holding portion of FIGS. 9A-9E.
Figure 10B:
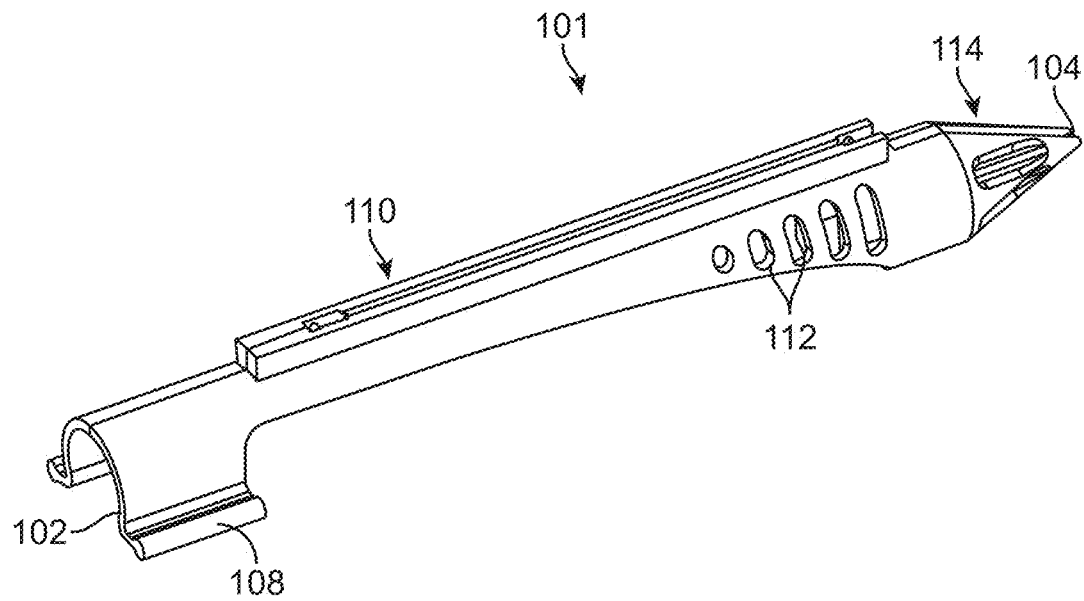

FIGS. 10A and 10B show the syringe holder 101 in different perspective views. The female luer connector 106 is best seen in FIG. 10A. The slider track 110 and needle housing 114 are best seen in FIG. 10B. The windows 112 are an optional feature and may be eliminated or may have any suitable shape, size and number, according to various embodiments.

Figure 11:
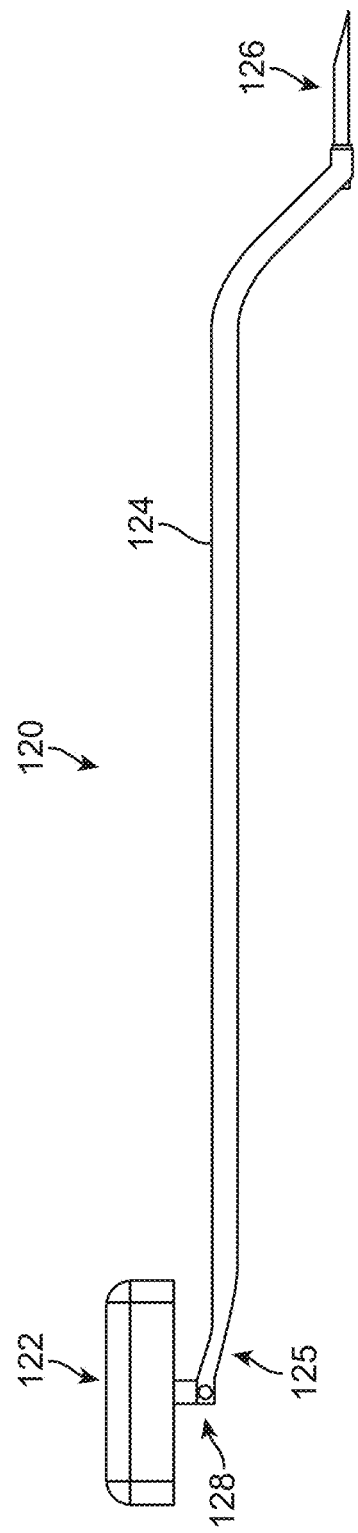
FIG. 11 is a side view of a needle holding portion of the needle cannula system of FIGS. 8A and 8B.

FIG. 11 is a side view of the needle holder 120. As described above, the needle holder 120 includes the thumb slider, which is attached to the support arm 124, which in turn is attached to the needle 126. Other features in this embodiment include a pin 128 to ride in the slot 111 on the slider track 110 and a flexible portion 125. The flexible portion 125 allows the thumb slider 122 to be pushed down, which pushes the pin 128 out of a locked position in the slider track 110 and allows the thumb slider 122 to advance along the slider track 110. There are two locks in the slot 111, at proximal and distal ends of the slider track 110, so that the needle holder 120 locks in a fully retracted position and a fully advanced position. The needle holder 120 may be made of any suitable material or combination of materials. For example, in some embodiments, all parts of the needle holder 120 are made of plastic or polymer, other than the needle 126, which is made of stainless steel or some other biocompatible metal.

Figure 12:
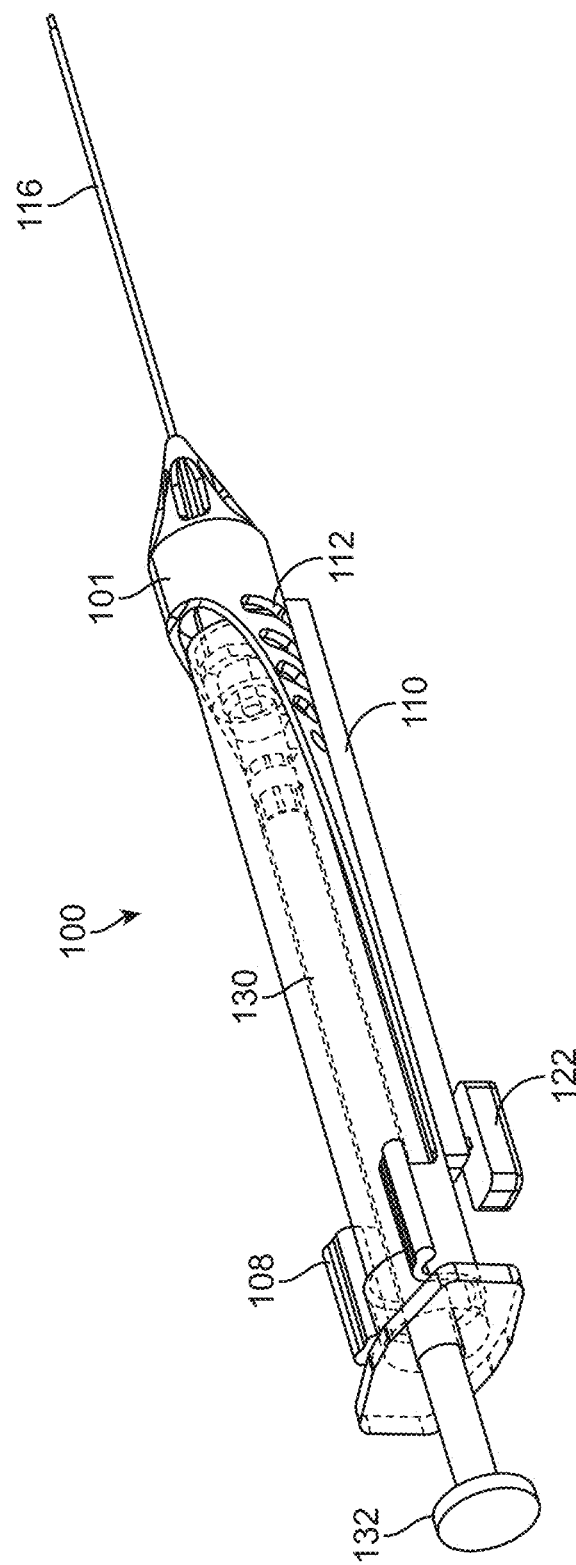
FIG. 12 is a bottom perspective view of the needle cannula system of FIGS. 8A and 8B, with a syringe and cannula attached.

FIG. 12 is a bottom perspective view of the needle cannula system 100, with a syringe 130 attached. The system 100 is configured to accommodate many different sizes and brands of syringes 130. In some embodiments, different sizes of syringe holders 101 may be provided to accommodate differently sized syringes 130.

Figure 13:
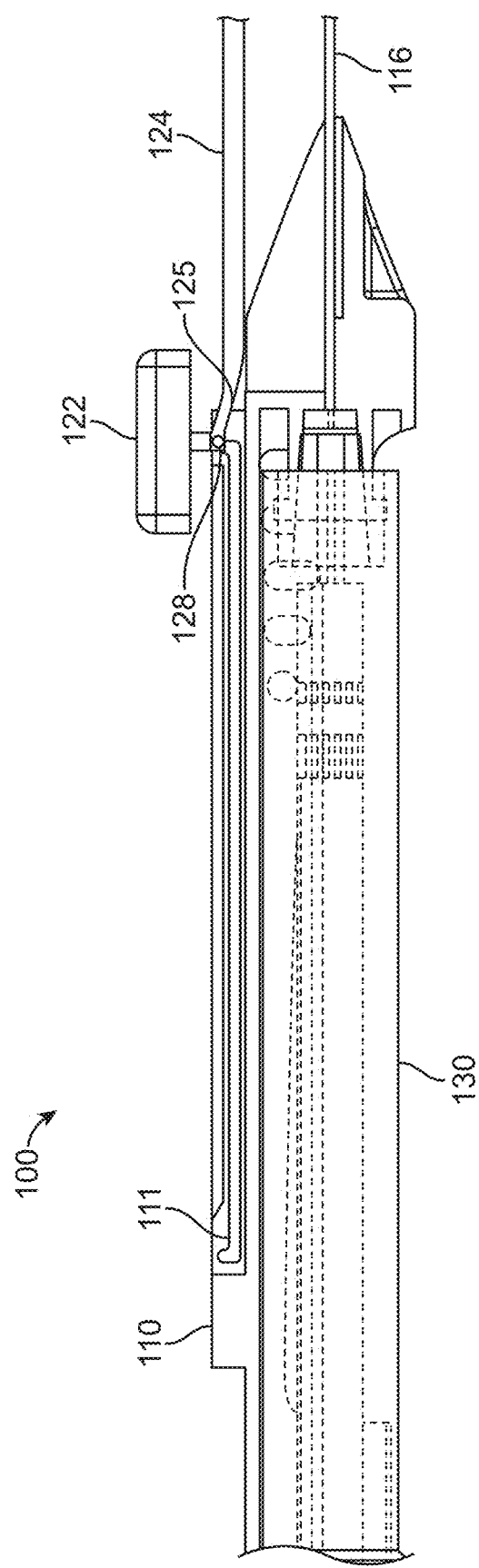
FIG. 13 is a side cross-sectional view of the needle cannula system of FIGS. 8A and 8B, with a syringe and cannula attached.

FIG. 13 is a side cross-sectional view of a distal portion of the needle cannula system 100, which better illustrates how the pin 128 of the needle holder 120 works within the slot 111 of the slider track 110. In FIG. 13, the thumb slider 122 is advanced to the forward or distal position, and the pin 128 resides within a small upwardly directed locking portion of the slot 111. The flexible portion 125 of the support arm 124 will move the pin 128 into the locked position when fully advanced as shown. This allows the user to manipulate the needle 126 (not shown) to puncture the epidermis while the needle 126 is locked in position and cannot accidentally slide proximally. Once the puncture is created, the user can depress the thumb slider 122, thus moving the pin 128 out of the locking portion of the slot 111, and slide the thumb slider 122 proximally to the proximal end of the slot 111, wherein there is a second upwardly directed locking portion. The needle holder 120 can thus be locked in a fully retracted position, so the user can manipulate the cannula 116 and perform an injection without fear of the needle 126 inadvertently leaving the needle housing 114 or advancing along the cannula 116. In alternative embodiments, this functionality may be achieved by one or more springs or other mechanisms for advancing, retracting and locking the needle holder 120. In one embodiment, for example, after the needle 126 is used to puncture the skin, the user may press a button on the syringe holder 101 to cause the needle 126 to fully retract. Alternatively or additionally, a spring may also be used to deploy the needle 126 to its fully advanced position.

Figure 14A:
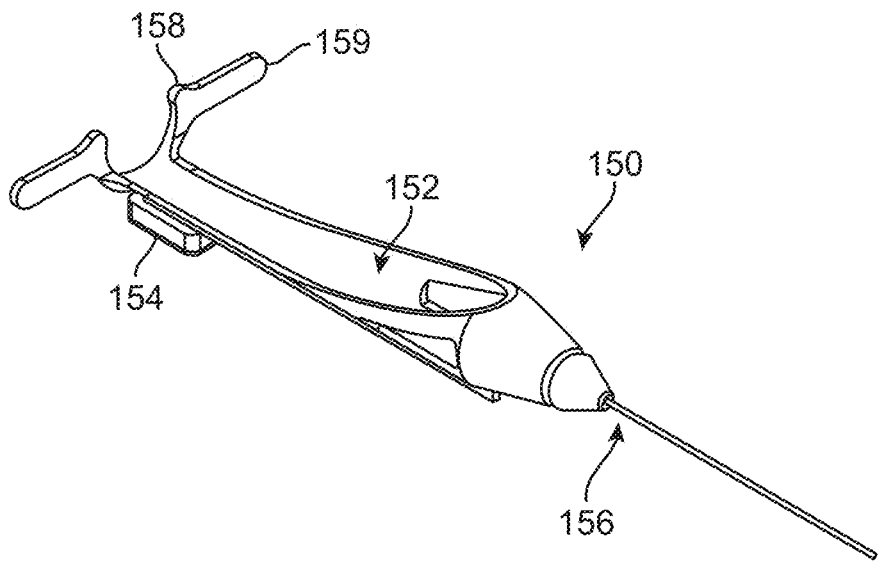
FIGS. 14A and 14B are bottom/front and bottom/rear perspective views, respectively, of a needle cannula system for performing injections, according to another alternative embodiment.
Figure 14B:
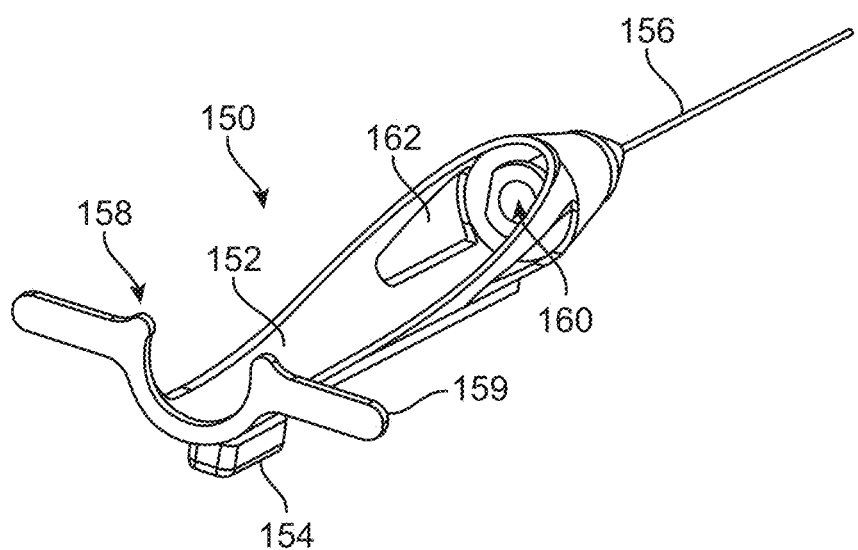
Figure 15:
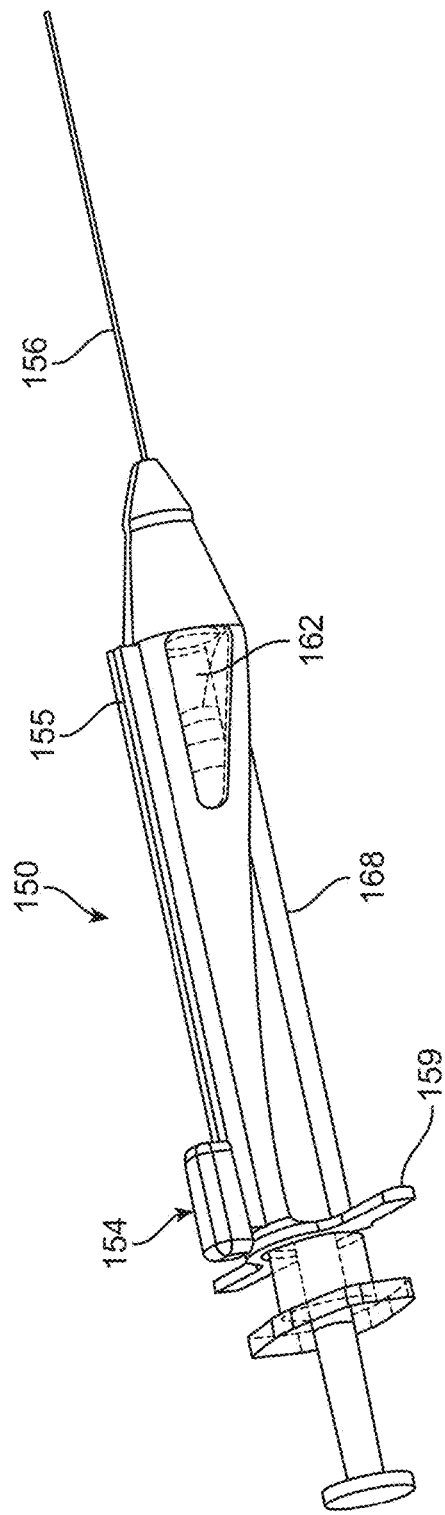
FIG. 15 is a perspective view of the needle cannula system of FIGS. 14A and 14B, with the needle retracted.
Figure 16:
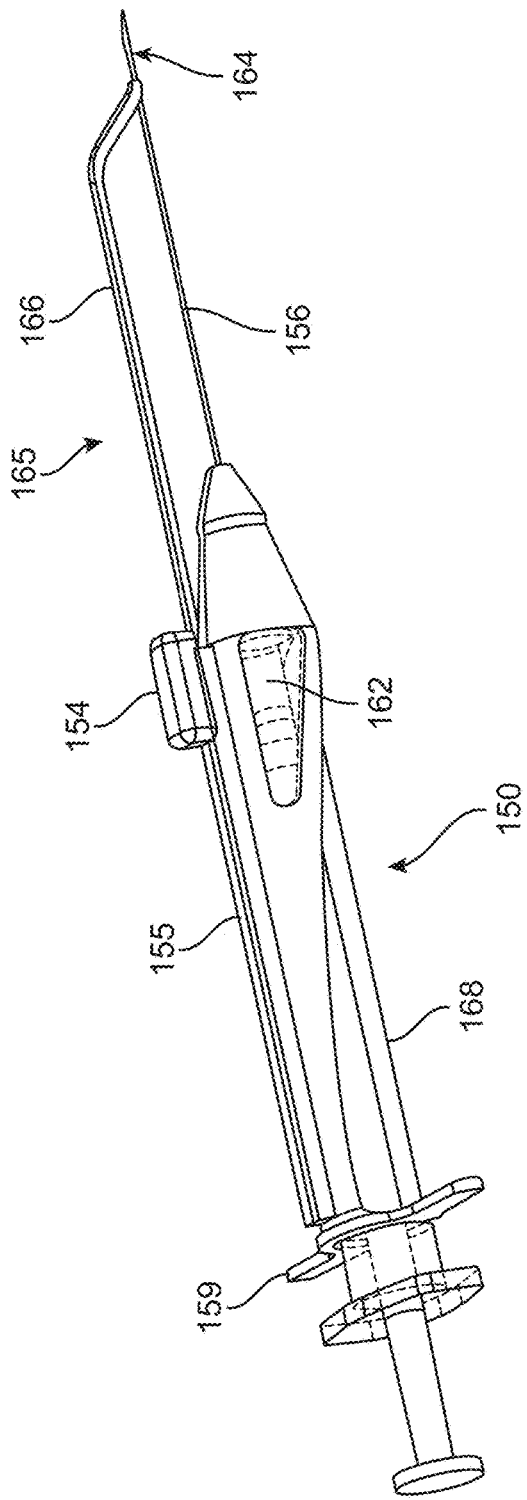
FIG. 16 is a perspective view of the needle cannula system of FIGS. 14A and 14B, with the needle advanced.

FIGS. 14A-16 illustrate an alternative embodiment of a needle cannula system 150, which is similar to the one described immediately above. In this embodiment, the needle cannula system 150 includes a syringe holder 152 and a needle holder 165. The syringe holder 152 includes a cannula 156, a proximal syringe clamp 158 with finger holds 159, a slider track 155, a female luer connector 160, and windows 162 to view the syringe and fluid within it. The needle holder 165 includes a thumb slider 154, a support arm 166, and a needle 164. FIGS. 14A and 14B show the needle cannula system 150 without a syringe attached and with the thumb slider 154 fully retracted proximally. FIG. 15 shows a syringe 168 attached to the needle cannula system 150 and the thumb slider 154 retracted proximally, so that the needle 164 is fully housed within the syringe holder 152. FIG. 16 shows the needle 164 fully advanced, in a position to create a puncture through the skin. Any of the features and functions of the embodiment of the needle cannula system 100 described above in relation to FIGS. 8A-13 may be applied to this alternative embodiment of the needle cannula system 150.

Figure 17A:
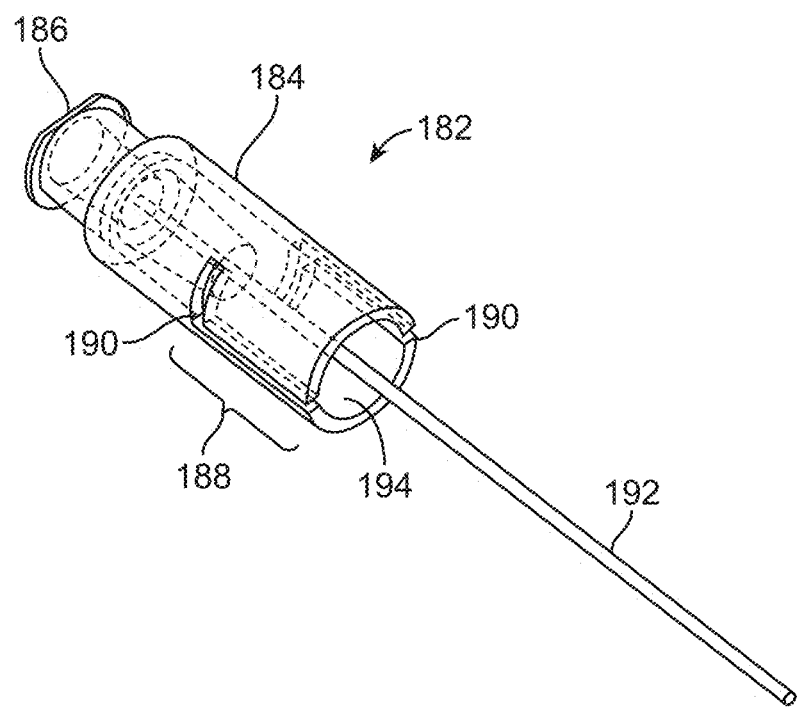
FIG. 17A is a perspective view of a cannula and hub portion of a needle cannula system for performing injections, according to another alternative embodiment.
Figure 17B:
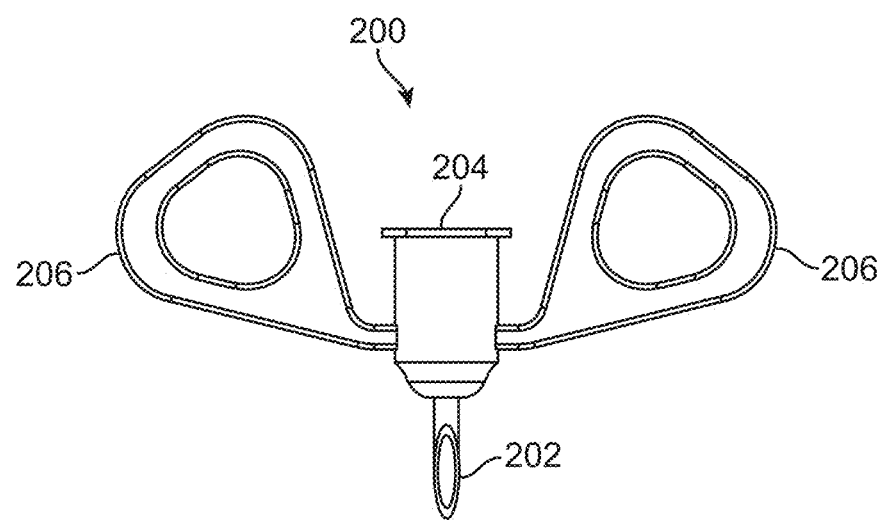
FIG. 17B is a top view of a needle portion of the needle cannula system that includes the cannula and hub portion of FIG. 17A.

Referring now to FIGS. 17A-20B, another alternative embodiment of a needle cannula system 180 is illustrated. The full system 180 is shown in FIGS. 20A and 20B. FIG. 17A is a perspective view of a cannula and hub portion 182 of the needle cannula system 180, and FIG. 17B is a top view of a needle portion 200 of the needle cannula system 180. Referring to FIG. 17A, the cannula and hub portion 182 includes a hub 184, a proximal luer connector 186, a sheathed section 188, a bilateral slot 190, a cannula 192 and a lumen 194. Referring to FIG. 17B, the needle portion 200 includes a luer connector portion 204, a needle 202, and two wings 206 attached to opposite sides of the luer connector portion 204.

Figure 18A:
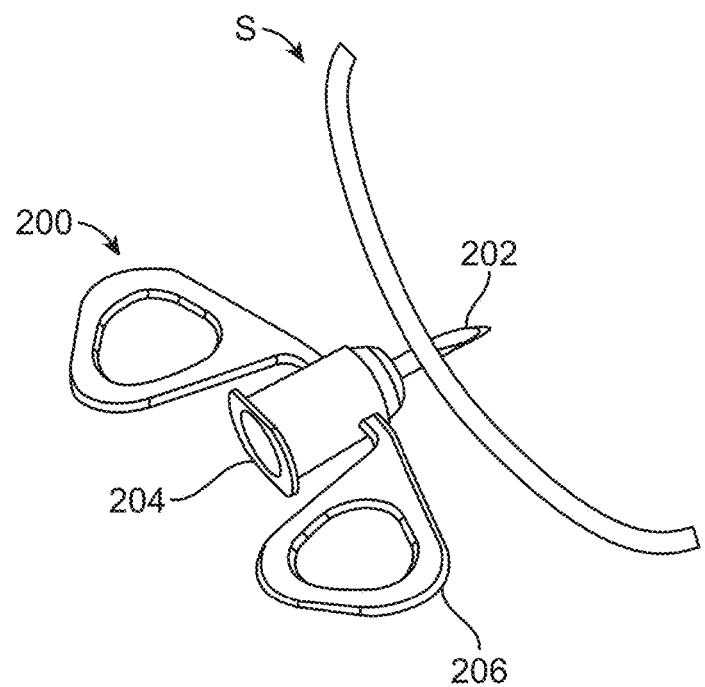
FIG. 18A is a perspective view of the needle portion of FIG. 17B, with the needle penetrating skin.
Figure 18B:
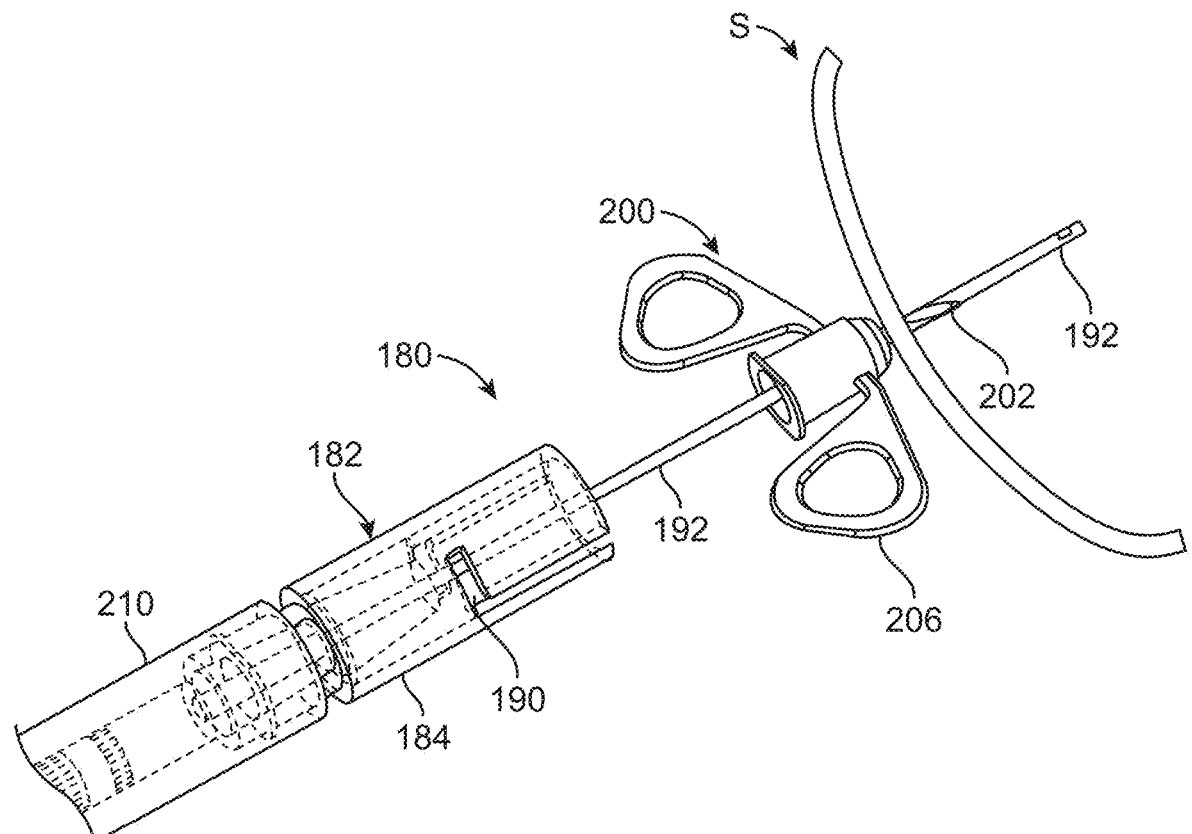
FIG. 18B is a perspective view of the needle portion penetrating skin as in FIG. 18A, and the cannula of the cannula and hub portion advanced through the needle portion.

FIGS. 18A-19B illustrate a method for using the needle cannula system 180. In FIG. 18A, the needle 202 of the needle portion 200 is first used to puncture the skin S, which may be the epidermis and optionally the dermis as well. As illustrated in FIG. 18B, the cannula 192 of the hub and cannula portion 182 is advanced through the luer connector portion 204 of the needle portion 200 and into the subdermal region of the patient. In this figure, the syringe 210 is attached to the hub 184.

Figure 19A:
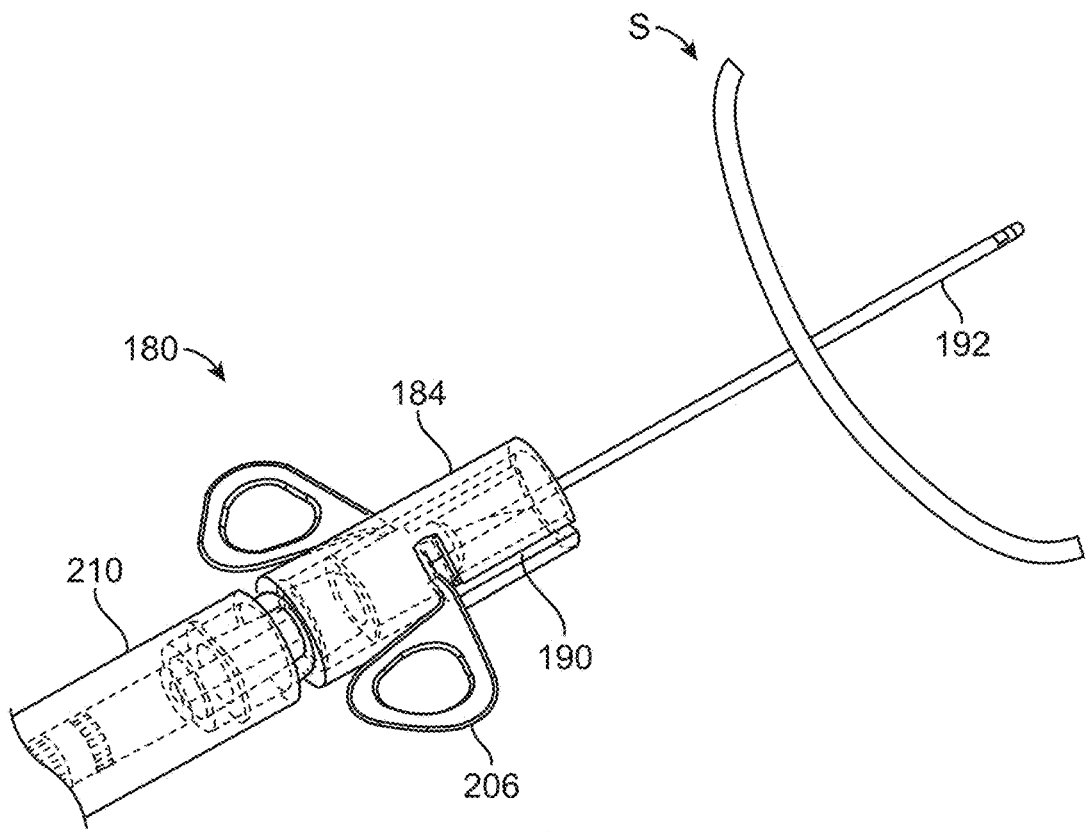
FIG. 19A is a perspective view of the needle cannula system of FIGS. 18A and 18B, with the needle portion retracted.
Figure 19B:
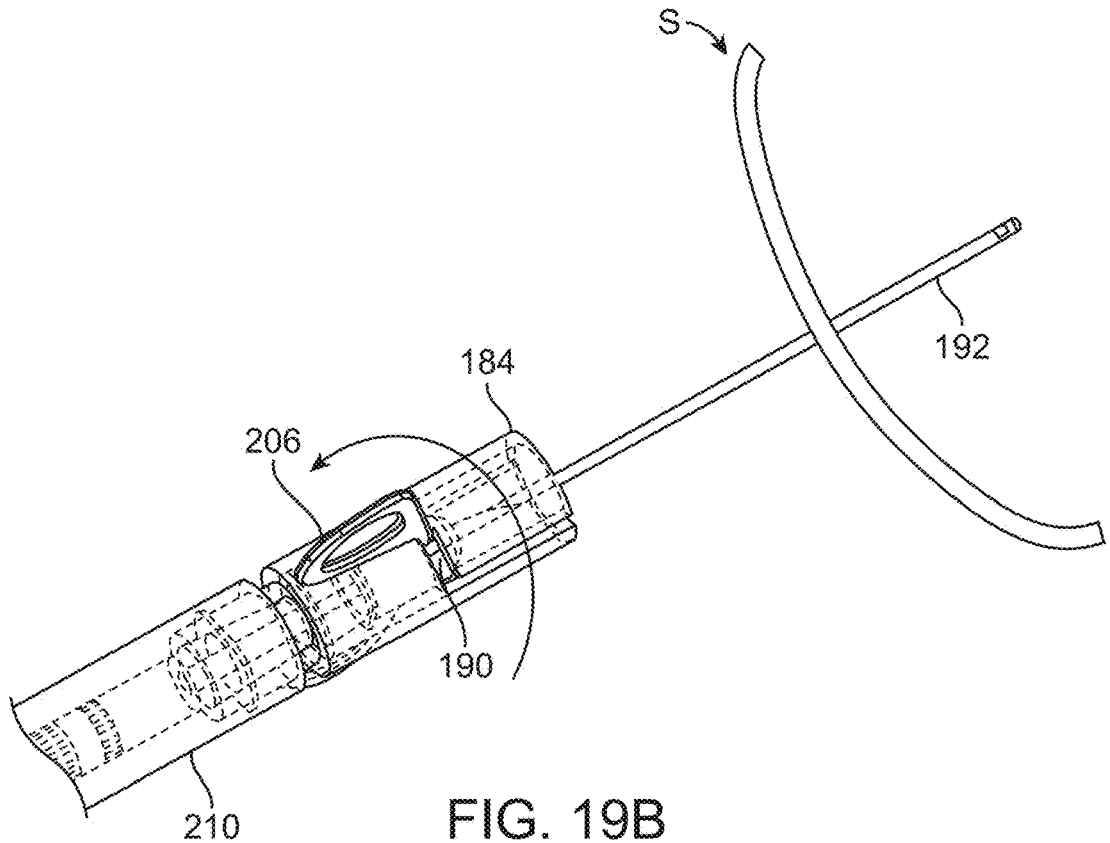
FIG. 19B is the same perspective view as in FIG. 19A, with the needle portion rotated to a locked position within the cannula and hub position.

FIG. 19A shows the needle portion 200 retracted back into the sheathed section 188 of the hub 184. The wings 206 fit into and through the bilateral slot 190. In FIG. 19B, the wings 206 are turned to rotate the needle portion 200 within the sheathed section 188, with the wings 206 passing along the bottom of the L-shaped bilateral slot 190. The L-shape of the slot 190 allows the wings 206 to lock in place, thus locking the needle portion 200 and keeping the needle 202 locked within the sheathed section 188. This keeps the needle 202 out of the way and thus prevents it from harming the physician or the patient while the physician performs the injection.

FIG. 20A shows the entirety of the needle cannula system 180 with the attached syringe 210 and with the needle portion 200 in the advanced/separated position relative to the hub and cannula portion 182. This is the configuration in which the needle portion 200 is used to puncture the skin. FIG. 20B shows the needle cannula system 180 and syringe 210 with the needle portion 200 fully retracted into the hub 184 and locked in position, to keep the needle 202 sheathed and protected. In various alternative embodiments, the wings 206 and/or the bilateral slot 190 may have other shapes and configurations.

Figure 21A:
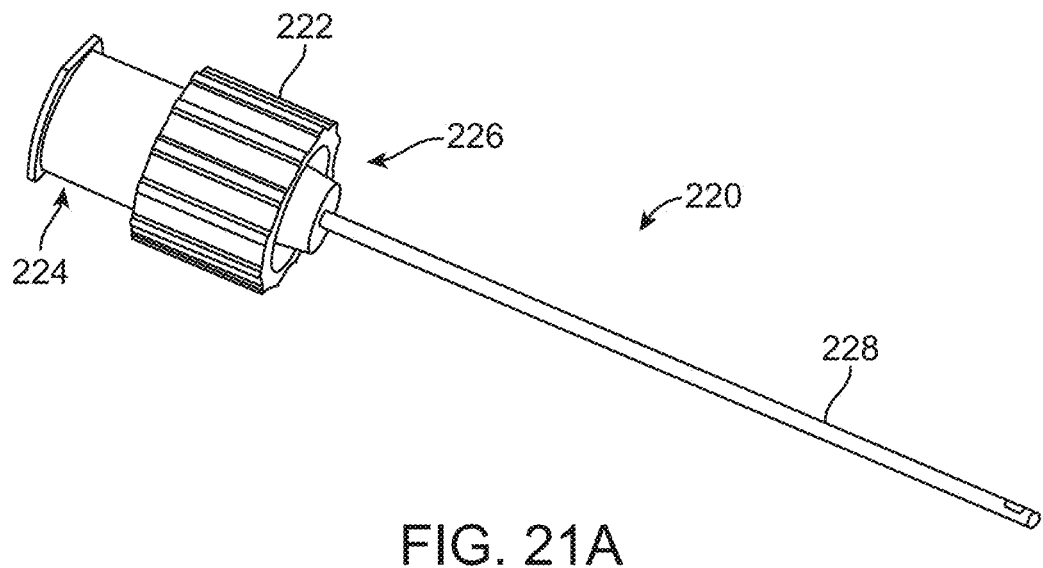
FIG. 21A is a perspective view of a cannula and hub portion of a needle cannula system for performing injections, according to another alternative embodiment.
Figure 21B:
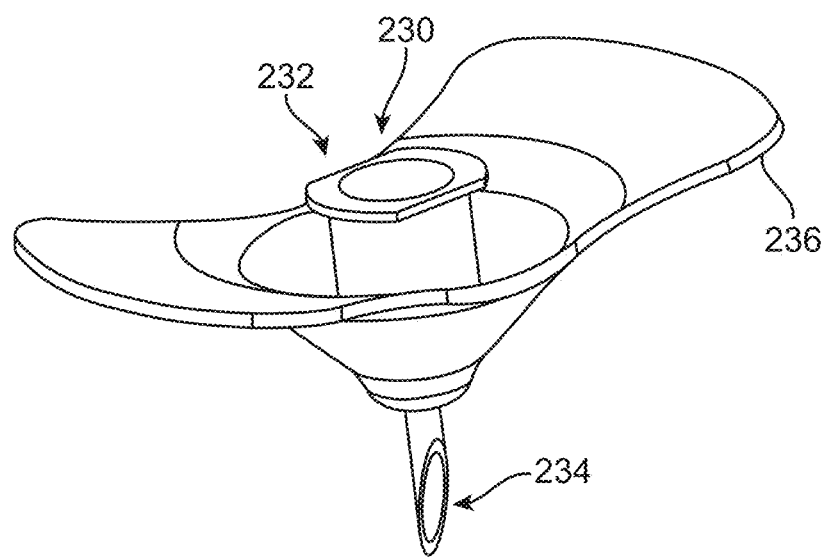
FIG. 21B is a perspective view of a needle portion of the needle cannula system that includes the cannula and hub portion of FIG. 21A.

FIG. 21A is a perspective view of a cannula and hub portion 220 of a needle cannula system for performing injections, according to another alternative embodiment. FIG. 21B is a perspective view of a needle portion 230 of the needle cannula system. In this embodiment, the cannula and hub portion 220 includes a hub 222 with a female male luer connector 224 facing proximally and a male luer connector 226 facing distally, and a cannula 228 attached to the distal end of the hub 222. The needle portion 230 includes a female luer connector 232, wings 236 and a needle 234. The operation of this needle/cannula system is illustrated in FIGS. 22A-22C.

Figure 22A:
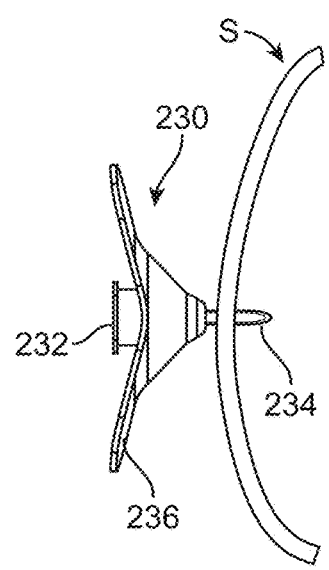
FIG. 22A is a side view of the needle portion of FIG. 21B, with the needle penetrating skin.
Figure 22B:
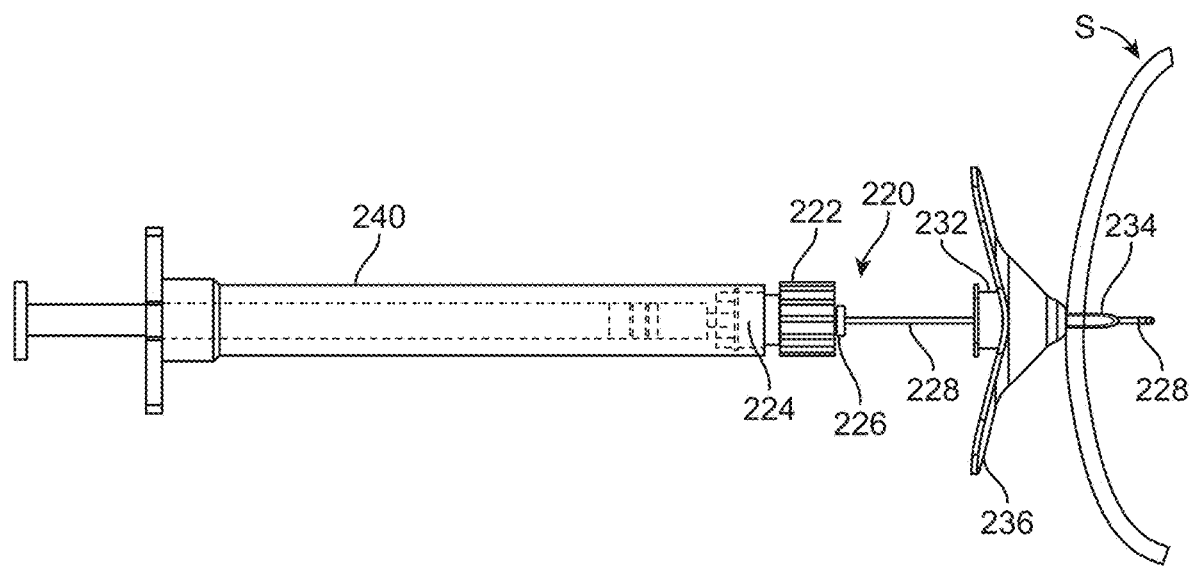
FIG. 22B is a side view of the needle portion penetrating skin as in FIG. 22A, and the cannula of the cannula and hub portion advanced through the needle portion.
Figure 22C:
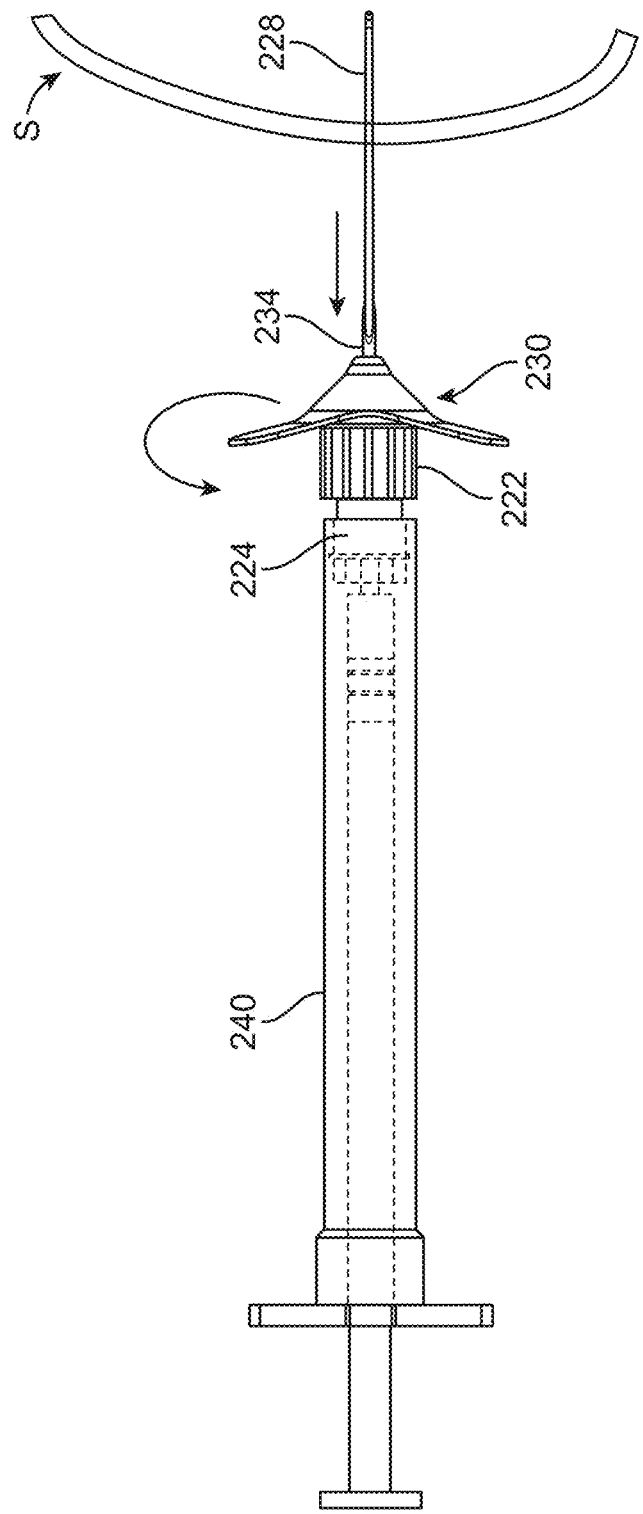
FIG. 22C is a side view of the needle cannula system as in FIG. 22B, with the needle portion retracted and attached to the cannula and hub portion.
Figure 23A:
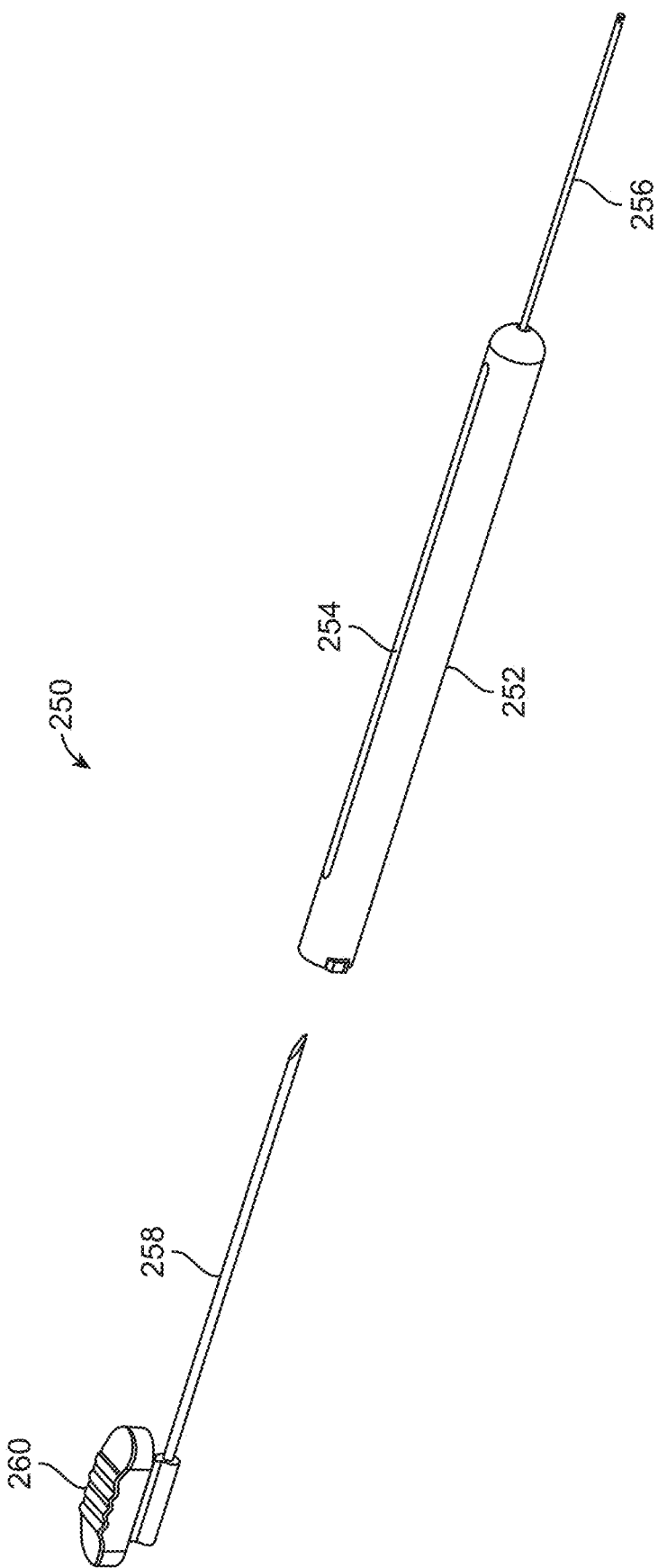
FIG. 23A is a perspective view of a needle cannula system for performing injections, according to another alternative embodiment.
Figure 23B:
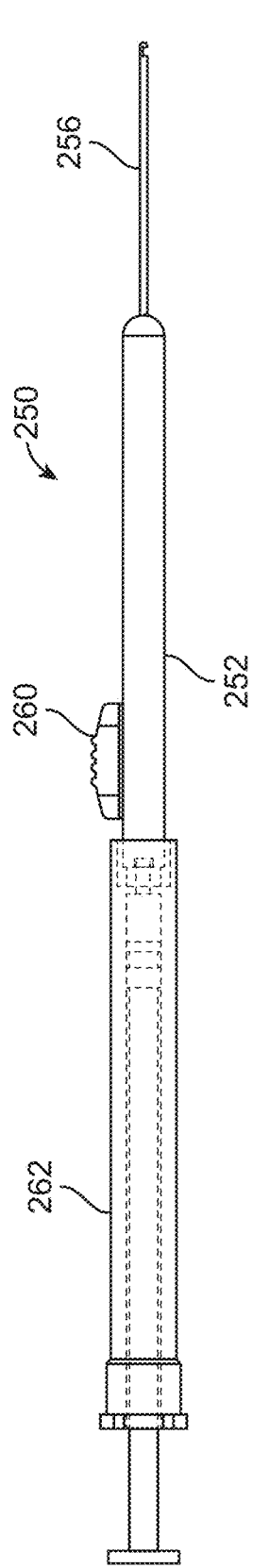
FIGS. 23B and 23C are side views of the needle cannula system of FIG. 23A, with the needle retracted (FIG. 23B) and the needle advanced (FIG. 23C); for performing injections, according to another alternative embodiment.
Figure 23C:
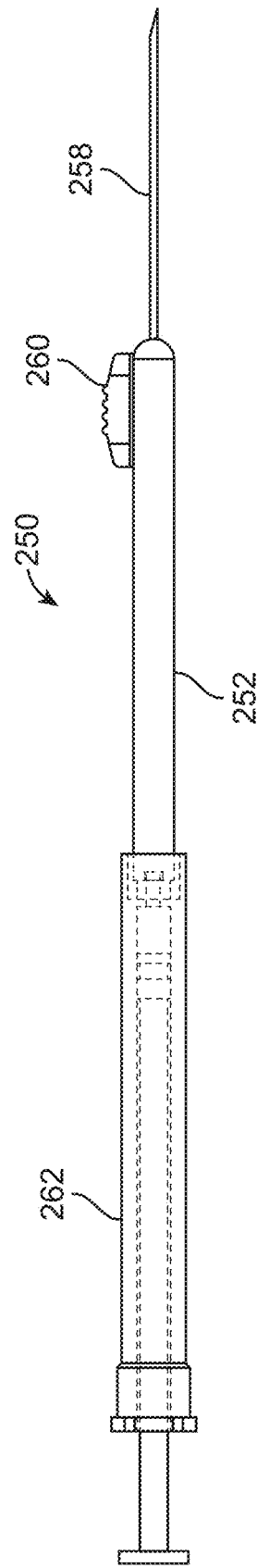

As illustrated in FIG. 22A, the user may use the needle 234 of the needle portion 230 to puncture the skin S (e.g., epidermis and in some cases dermis). The wings 236 may be used for conveniently holding and manipulating the needle portion 230. As shown in FIG. 22B, as a next step, the cannula and hub portion 220 may be attached to a syringe 240, and the cannula 228 of the cannula and hub portion 220 may be inserted through the needle 234 of the needle portion 230, into the subdermal (or other) space under the skin S. Next, as in FIG. 22C, the needle portion 230 may be pulled back over the cannula 228, and the female luer connector 232 of the needle portion 230 may be locked with the male luer connector 226 of the cannula and hub portion 220 (curved arrow). The user may then advance and manipulate the cannula 228 with the needle 234 is positioned back away from the skin S. When the cannula 228 is in a desired position, the injection may be performed. is a side view of the needle portion of FIG. 21B, with the needle penetrating skin;

FIGS. 23A-23C illustrate another embodiment of a needle cannula system 250 for performing injections. Referring to FIG. 23A, which is a disassembled view, the needle cannula system 250 includes a tubular shaft 252 with a slot 254 and a cannula attached to its distal end, and a needle 258 with a slider 260 attached to its proximal end. FIGS. 23B and 23C show the needle cannula system 250 assembled, with a syringe 262 attached to its proximal end. In FIG. 23B, the slider 260 is in a proximal position to position the needle 258 fully within the tubular shaft 252 and to expose the cannula 256. In FIG. 23C, the slider 260 has been advanced distally along the slot 254 (not visible in this figure) to advance the needle 258 over the cannula 256. The user may puncture the patient's skin with the needle slider 260 and the needle 258 advanced, as in FIG. 23C, and then retract the needle 258 to the position shown in FIG. 23B for manipulation and positioning of the cannula 256 and for the injection. The needle may be advanced and retracted as many times as necessary to fully treat a patient.

Figure 24:
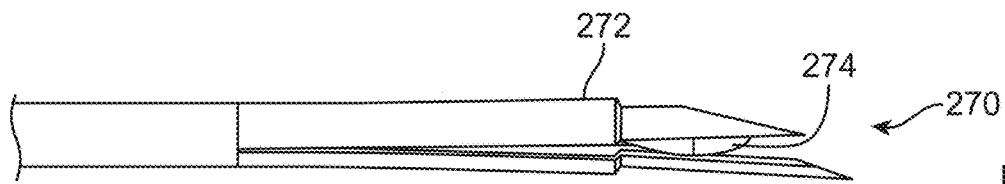
FIG. 24 is a side view of a distal end of a needle cannula system with a split needle and internal cannula, according to another alternative embodiment.

FIG. 24 is a side view of a distal end of a needle cannula system 270 according to yet another embodiment. In this embodiment, the needle cannula system 270 includes a split needle 272 with an internal cannula 274. The split needle 272 is used to puncture the skin, and the internal cannula 274 is then advanced through the split needle 272 to enter the patient and perform the injection.

Figure 25:
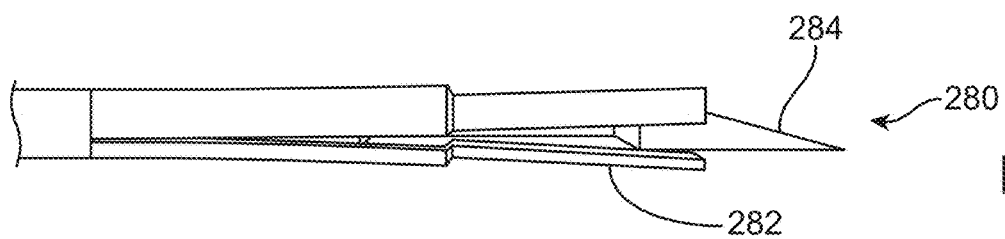
FIG. 25 is a side view of a distal end of a needle cannula system with a split cannula and internal needle, according to another alternative embodiment.

FIG. 25 is a side view of a distal end of a needle cannula system 280 according to another alternative embodiment, which is somewhat like the reverse of the system 270 of FIG. 24. In this embodiment, the needle cannula system 280 includes a split cannula 282 and an internal needle 284. In use, the needle 284 is first placed in advanced position, protruding outside of the distal end of the split cannula 282.

In this configuration, the needle cannula system 280 is used to pierce the skin. The internal needle 284 is then drawn proximally inside the split cannula 282, and the split cannula 282 is positioned under the skin as desired and used for the injection.

Figure 26:
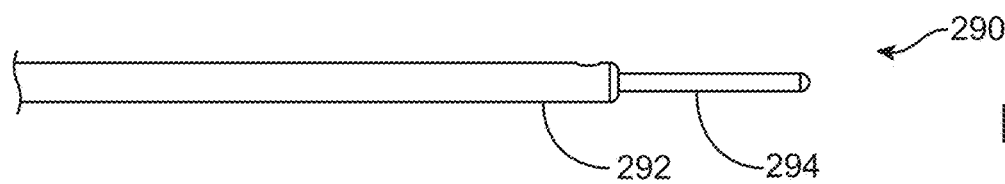
FIG. 26 is a side view of a distal end of a needle cannula system with a guidewire and a side-facing cannula, according to another alternative embodiment.

FIG. 26 is a side view of a distal end of another alternative embodiment of a needle cannula system 290. In this embodiment, the needle cannula system 290 includes a cannula 292 with a side-facing injection port and a guidewire 294 that passes through the lumen of the cannula 292. The guidewire 294 can be used for accessing and positioning beneath the patient's skin, and the cannula 292 may then be advanced into position over the guidewire 294.

Figure 27:
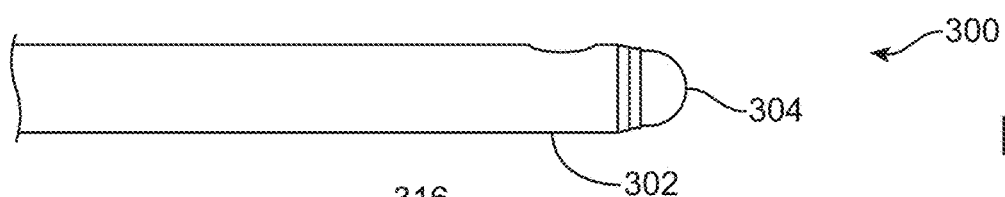
FIG. 27 is a side view of a distal end of a needle cannula system with a blunt tip and a side-facing cannula, according to another alternative embodiment.

FIG. 27 illustrates another embodiment of a needle cannula system 300. In this embodiment, the needle cannula system 300 includes a cannula 302 with a side-facing injection port and a guidewire with a blunt distal tip 304. The blunt distal tip 304 may be used as an obturator to help advance the cannula 302 into position beneath the skin. Injectable material may then be injected through the side port of the cannula 302.

Figure 28:
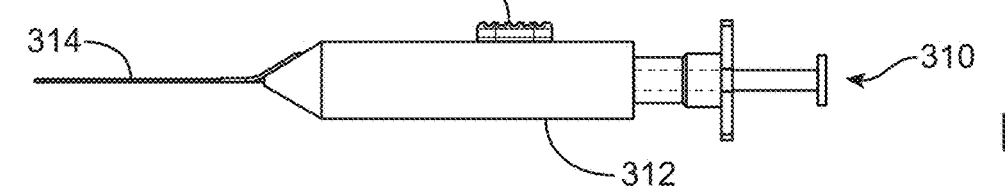
FIG. 28 is a side view of a needle cannula system with a syringe housing and a built-in cannula, according to another alternative embodiment.

FIG. 28 shows yet another alternative embodiment of a needle cannula system 310, which includes a housing 312 attached to a cannula 314 and a slider 316 attached to a retractable needle (not visible). The slider 316 slides back and forth along the housing 312, through a slot, to advance and retract the needle for puncturing the skin.

Figure 29:
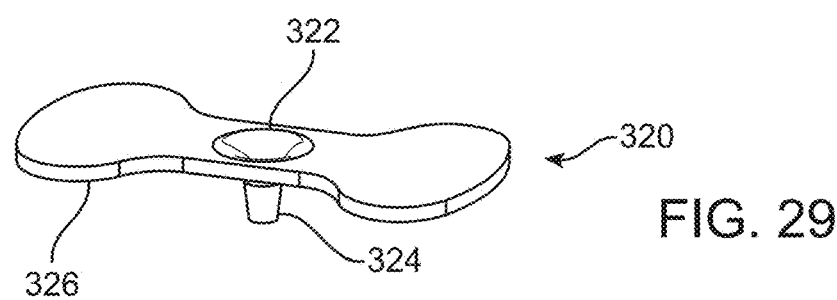
FIG. 29 is a perspective view of a skin port for passing a cannula through epidermis, according to one embodiment.

FIG. 29 is a perspective view of a skin port device 320 for passing a cannula through the skin, according to one embodiment. The skin port device 320 may be made of any suitable material, such as but not limited to plastic or other polymers. The skin port device 320 may include an aperture 322, through which a cannula is passed, a protrusion 324 for passing through the skin, and two wings 326 for holding the device 320 and maintaining its position on the patient's skin. In some embodiments, the skin-facing side of the wings 326 may be partially or completely covered with an adhesive material, which may optionally be covered with a tape or the like before use. The skin port device 320 may be used to form and/or maintain a puncture through the skin, to allow passage of a cannula through the aperture 322. Thus, the skin port device 320 may be provided by itself or with a cannula device to facilitate access and injection.

Figure 30:
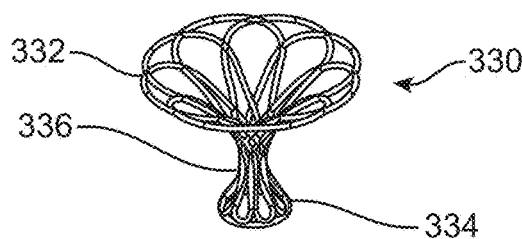
FIG. 30 is a perspective view of a skin port for passing a cannula through epidermis, according to an alternative embodiment.

FIG. 30 is a perspective view of an alternative embodiment of a skin port device 330. In this embodiment, the skin port device 330 is made of an expandable metal, such as but not limited to Nitinol. The skin port device 330 includes a skin surface portion 332, a below skin portion 334, and a through channel portion 336. The skin surface portion 332 is wider (has a larger diameter) than the below skin portion 334, so the skin surface portion 332 can stabilize on the outer skin surface and prevent the skin port device 330 from passing through the puncture hole. The below skin portion 334 changes from a constricted, narrow configuration for delivery below the skin to the expanded, wider configuration shown in FIG. 30. The below skin portion 334 in the expanded configuration helps prevent the skin port device from popping out of the skin. The channel portion 336 has a lumen that allows for passage of a cannula through the skin port device 330 and thus through the skin.

Referring now to FIGS. 31A-31C, another embodiment of a needle and cannula device 340 is illustrated in top view (FIG. 31A), side view (FIG. 31B) and front view (FIG. 31C). In this embodiment, the needle and cannula device 340 includes a syringe holder 342 with a protective, cone-shaped needle guard 346 (or "needle housing"), a slider 344 and a cannula 348. (Other parts of the needle and cannula device 340 are described in relation to later figures, where those parts are visible.) The slider 344 includes a proximal finger stop feature 352 and a distal finger stop feature 354, either or both of which may be used to move the slider 344 proximally and distally along the syringe holder 342. A support arm 356 (FIGS. 31B and 31C) extends distally from the distal finger stop feature 354 and connects to a needle (not visible), which is slidably mounted over the cannula 348. In these figures, a syringe 350 is shown inserted into the needle and cannula device 340. However, the syringe 350 is typically not part of the device 340 but instead may be any suitable syringe used for injections. In some embodiments, a custom syringe may be included as part of a needle and cannula device, but in other embodiments the syringe 350 is provided separately and is not part of the device 340. According to various embodiments, the needle and cannula device 340 may be sized and shaped to accommodate any suitable syringe 350.

The various part of the needle and cannula device 340 may have any of a number of suitable dimensions, so the dimensions listed in this application are only examples. For example, in some embodiments, the syringe holder 342 may have a width of between about 10 mm and about 15 mm, or in the embodiment shown about 12.5 mm. The needle of the device 340 may have a length of between about 3 mm and about 7 mm, or in the embodiment shown about 5 mm. The slider 344, as measured from a proximal side of the proximal finger stop feature 352 to a distal side of the distal finger stop feature 354, may have a length of between about 20 mm and about 40 mm, or in the embodiment shown about 30 mm. The entire length of the syringe holder 342, including the conical needle guard 346, may have a length of between about 110 mm and about 125 mm, or in the embodiment shown about 117.5 mm. The cannula 348 may extend out of the needle guard 346 a distance of between about 30 mm and about 40 mm, or in the embodiment shown about 36 mm. Again, these dimensions are examples only.

In some embodiments, the hub of the cannula 348 or the syringe holder 342 may include one or more orientation markings 343 or features, such as one or more dots, lines, etc., to indicate the direction in which the opening of the cannula is pointing. Such markings 343 or features may be positioned on the same side that the opening in the distal portion of the cannula 348 and the bevel of the sharp distal tip 361 are facing or may be positioned on the opposite side. In the embodiment shown in FIGS. 31A and 31B, the marking 343 is a dot on the syringe holder 342, on the opposite side from the slider 344 and the opening of the cannula 348. In alternative embodiments, multiple markings, different markings, alternative placements of markings and/or surface features indicating directionality may be used.

Figure 32:
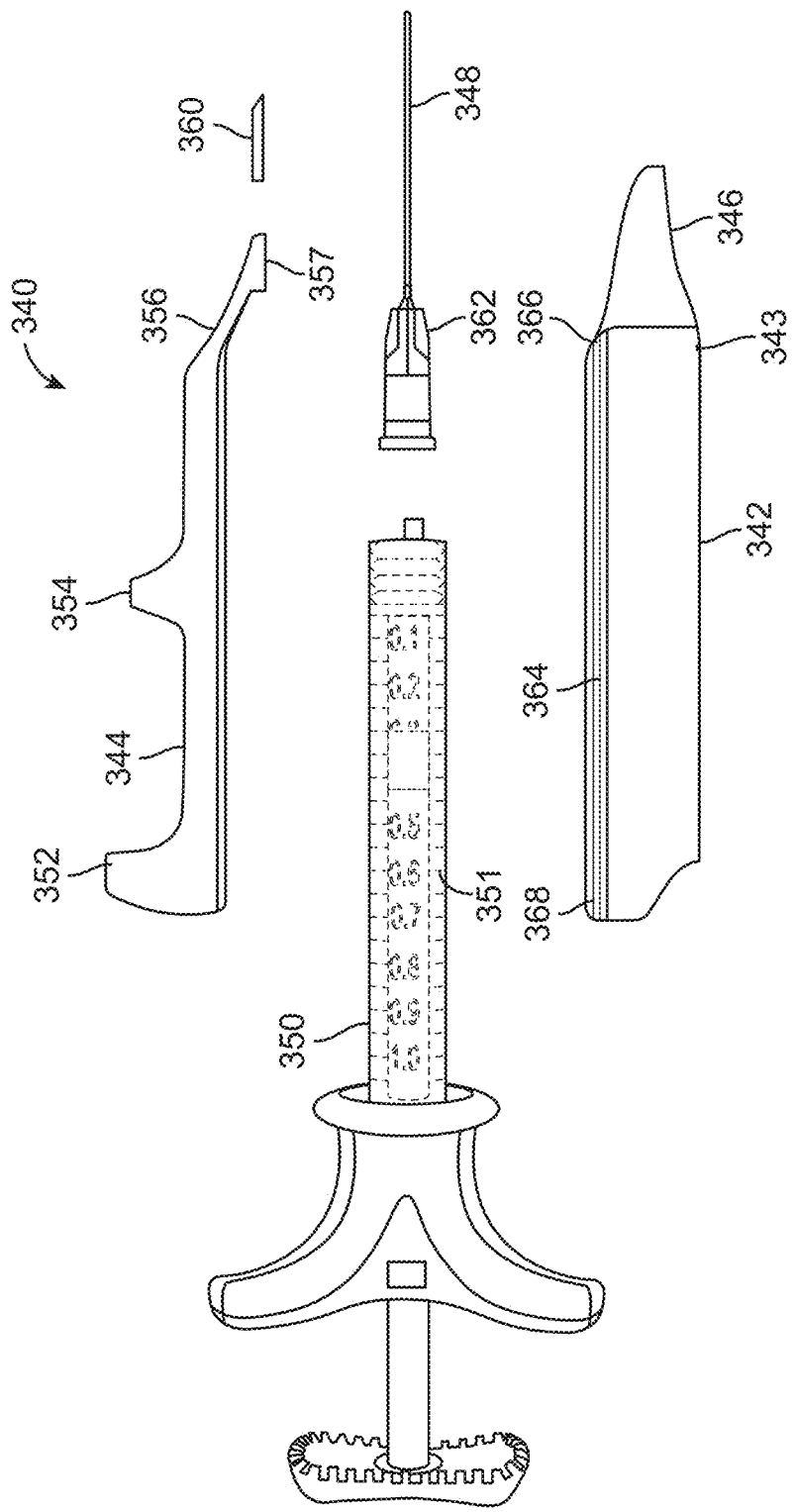
FIG. 32 is an exploded view of the needle and cannula device of FIGS. 31A-31C, with the syringe.

Referring now to FIG. 32, the needle and cannula device 340 is shown in exploded view. The syringe 350 is also shown, but for illustrative purposes only. The syringe 350 is not part of the needle and cannula device 340 in this embodiment, and other syringes may be used with the needle and cannula device 340. As shown in this example, the barrel of the syringe 350 includes multiple fluid level markings 351, as is common. The syringe holder 342 is made of a transparent (or at least partially transparent) material, such as glass or clear plastic, so the fluid markings 351 on the syringe 350 can be viewed by the user during use of the device 340.

All of the parts of the needle and cannula device 340 can be seen in FIG. 32. There is a needle carriage portion, which includes the slider 344, the two finger stop features 352, 354, and the support arm 356, which has a needle attachment portion 357 into which the needle 360 attaches. The syringe holder 342 includes the cone-shaped needle guard 346 and a track 364 with a distal end 366 and a proximal end 368. The slider 344 is attached to, and slides along, the track 364. Typically, the track 364 includes a proximal locking feature at the proximal end 368 and a distal locking feature at the distal end 366, which lock the slider 344 in a proximal position and a distal position, respectively. The proximal position places the needle 360 in a retracted location safely within the needle guard 346. The distal position places the needle 360 in an extended location, over the cannula 348 with the sharp tip of the needle 360 positioned at or immediately adjacent the distal end of the cannula 348. In the locked/extended position, the needle 360 and the distal end of the cannula 348 may be introduced through the skin together. The needle 360 is then retracted proximally to the retracted position, where it is housed safely inside the needle guard 346. In this example, the syringe holder 342, the needle guard 346 and the track 366 are all one piece. In alternative embodiments, they may be two of more assembled pieces.

The cannula 348 may be attached to a cannula hub 362, which has a Luer lock at one end that attaches to mating features of the syringe 350. The hub 362 fits inside the syringe holder 342. As mentioned above, the syringe holder 342 may be entirely or partially transparent, at least enough so a user can see fluid level markings on a syringe 350 placed within the syringe holder 342.

Figure 33A:
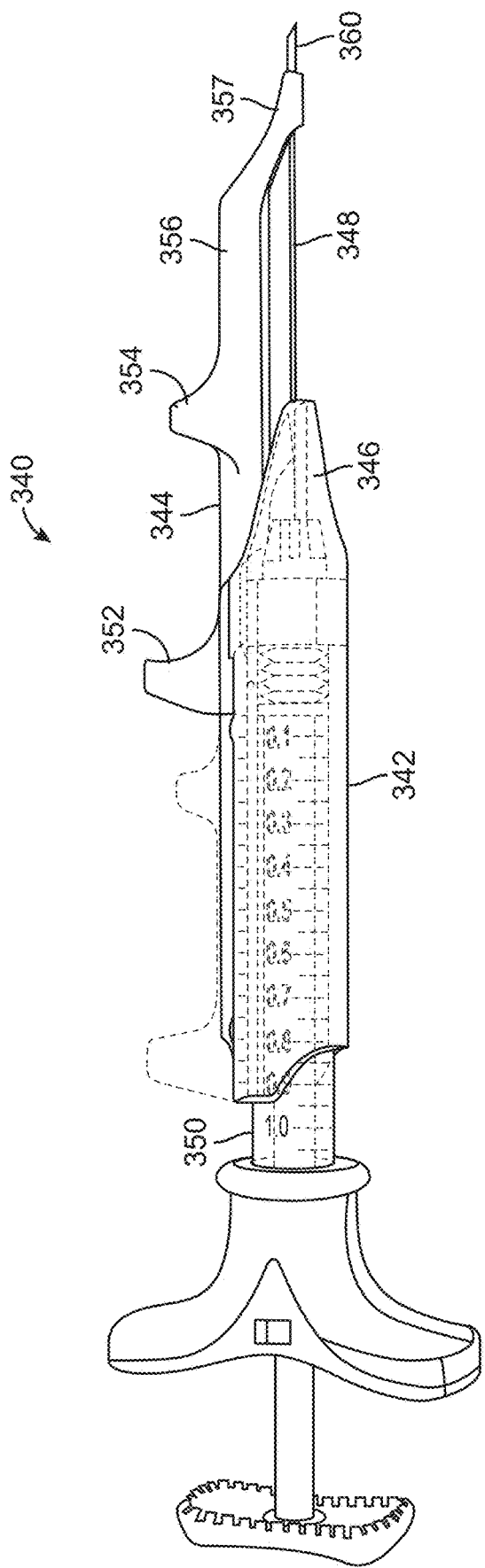
FIG. 33A is a side view of the needle and cannula device of FIGS. 31A-32, illustrating advancement of a needle carriage portion of the device, according to one embodiment.

FIG. 33A is a side, assembled view of the needle and cannula device 340, illustrating the travel distance of the slider 344 from the proximal/retracted position (dotted lines) to the distal/extended position. The travel distance of the needle carriage portion of the device 340 (i.e., the slider 344, the support arm 356, and the needle 360) may range from about 30 mm to about 60 mm in various embodiments. In the embodiment shown, the travel distance is about 45 mm. In use, to retract the needle 360, the user might use the proximal finger stop feature 352 to slide the slider 344 a first portion of the travel distance and might then use the distal finger stop feature 354 to slide the slider 344 a second portion of the travel distance. Or the user might do the opposite. One purpose of the two finger stop features 352, 354 is to allow the user to easily and comfortably slide the slider the full distance proximally and distally along the syringe holder 342.

Figure 33B:
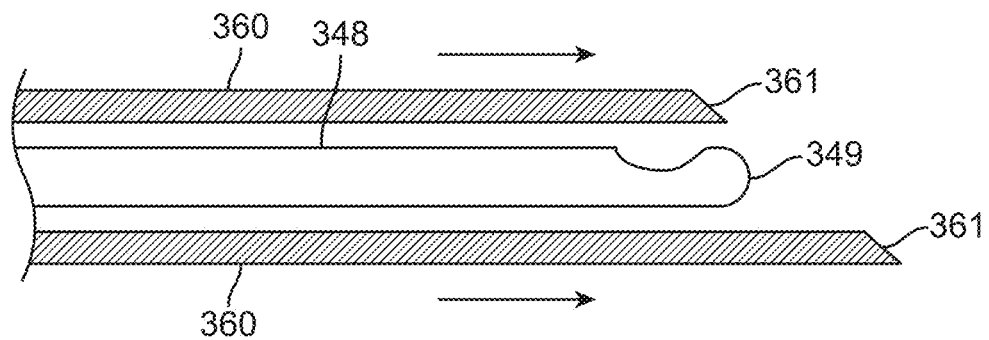
FIGS. 33B and 33C are side, partial cross-sectional views of a distal portion of the needle and cannula device of FIGS. 31A-33A, illustrating retraction of the needle relative to the cannula.
Figure 33C:
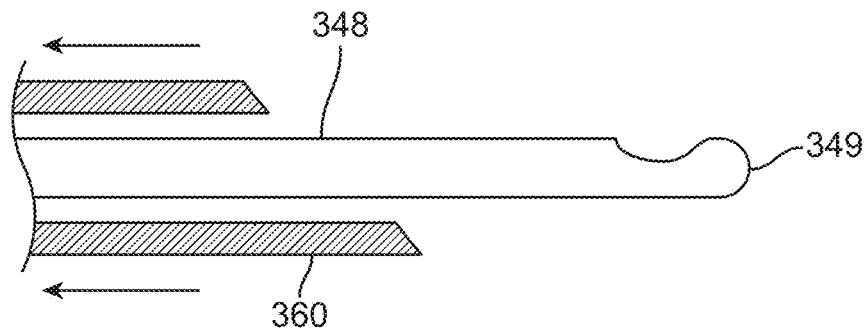

Referring to FIGS. 33B and 33C, a more detailed view of distal portions of the needle 360 and the cannula 348 are shown. In FIG. 33B, the sharp distal tip 361 of the needle 360 is advanced to the extended (or "distal") position, where it is located at or immediately adjacent the blunt distal tip 349 of the cannula 348. When the needle 360 and the cannula 348 are in this position relative to one another, they may be advanced together through the epidermis and optionally the dermis of the skin, as represented by the solid-tipped arrows in FIG. 33B. In this position, the opening in the distal portion of the cannula 348 and the bevel of the sharp distal tip 361 both face upwards, in the same direction. In alternative embodiments, the opening in the distal portion of the cannula 348 and the bevel of the sharp distal tip 361 both face downwards. Once both the needle 360 and the cannula 348 have been advanced through the skin, the needle 360 is retracted, as illustrated in FIG. 33C, leaving the cannula 348 in place below the epidermis and in some cases below the dermis. In some cases, the user may push on the needle and cannula device as a whole while retracting the needle 360, to ensure that the cannula blunt tip 349 remains under the skin. In some embodiments, the needle 360 may automatically retract via the press of a button or even by way of an electronic mechanism.

Figure 34:
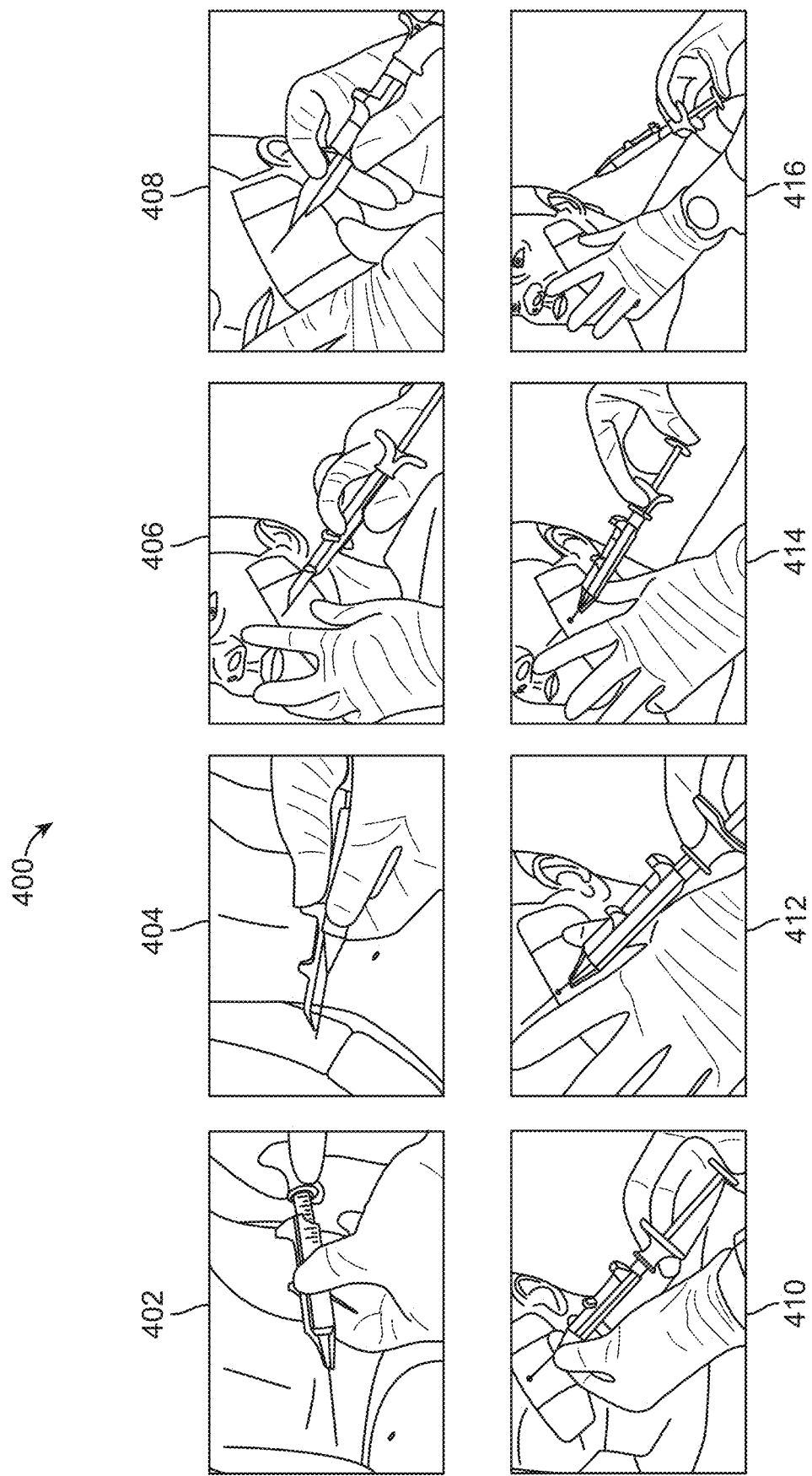
FIG. 34 is a multi-panel illustration of a method of performing an injection, using a needle and cannula device of the present disclosure, according to one embodiment.

Referring now to FIG. 34, an example injection method 400 for injecting a dermal filler or other substance into or below the skin is illustrated. In this method, a syringe is first installed into a needle and cannula device 402. This may be done, for example, by inserting the syringe into the proximal end of the device and twisting the distal end of the syringe barrel onto a Luer lock feature inside the syringe holder of the needle and cannula device. Other embodiments may have a side loading configuration. Next, the user slides the slider forward (distally) 404 to place the needle in the extended position, in which the sharp tip of the needle is located at or immediately adjacent the blunt distal end of the cannula. In many embodiments, the needle and cannula device includes a locking feature to lock the slider, and thus the needle, in the extended/distal position.

Once the needle is in the extended position, the user advances the needle tip and the blunt cannula tip through the patient's skin 406, for example the skin of the face as shown in the drawings. In some embodiments, the needle tip is advanced to a location below the dermis. Next, the user retracts the needle 408, leaving cannula in place in the skin. In some cases, the user may push slightly on the syringe holder to keep the cannula below the skin while sliding the slider proximally to retract the needle. This will help keep the cannula tip in the skin during needle retraction. The needle is retracted all the way back, until it is housed completely within the needle guard (or "housing"), thus preventing the user or the patient from being exposed to the sharp tip. The slider and the track of the needle and cannula device will usually include a locking feature, to lock the slider in the proximal position and thus lock the needle in the needle guard. To release the slider from the proximal and distal locking features, the needle and cannula device may include an unlocking feature, such as a button, a pinch release or a mechanism that unlocks the slider when the slider is pushed downward. Any suitable locking and unlocking features may be included, according to various embodiments.

After locking the needle in the safe position within the needle guard/housing, the user may stabilize the device 410 and/or adjust her grip on the device. The user may then advance the cannula further into the skin 412 to position the distal tip of the cannula at a desired target location. The user then presses the syringe plunger 414 to inject the filler or other substance. Optionally, the user may reposition the cannula tip within the patient and inject additional substance as many times and in as many target locations as desired, without removing the cannula from the skin. Finally, when the injection is complete, the user removes the cannula from the patient 416. The user may then slide the slider forward (distally) again, to place the needle in the extended position, and the method steps may be repeated as many times as desired, for example when injecting multiple syringes of a substance into different locations on the same patient. For sterility and safety purposes, the needle and cannula device should be used only on one patient for one procedure and is meant to be disposed of after one procedure. In some embodiments, the sharpness and durability of the needle tip may dictate a maximum number of injections per one device. For example, in some embodiments the device may be used only for two injections on the same patient, while in other embodiments, three, four, five, or even as many as six or eight injections may be performed on the same patient with the same device.

Figure 35:
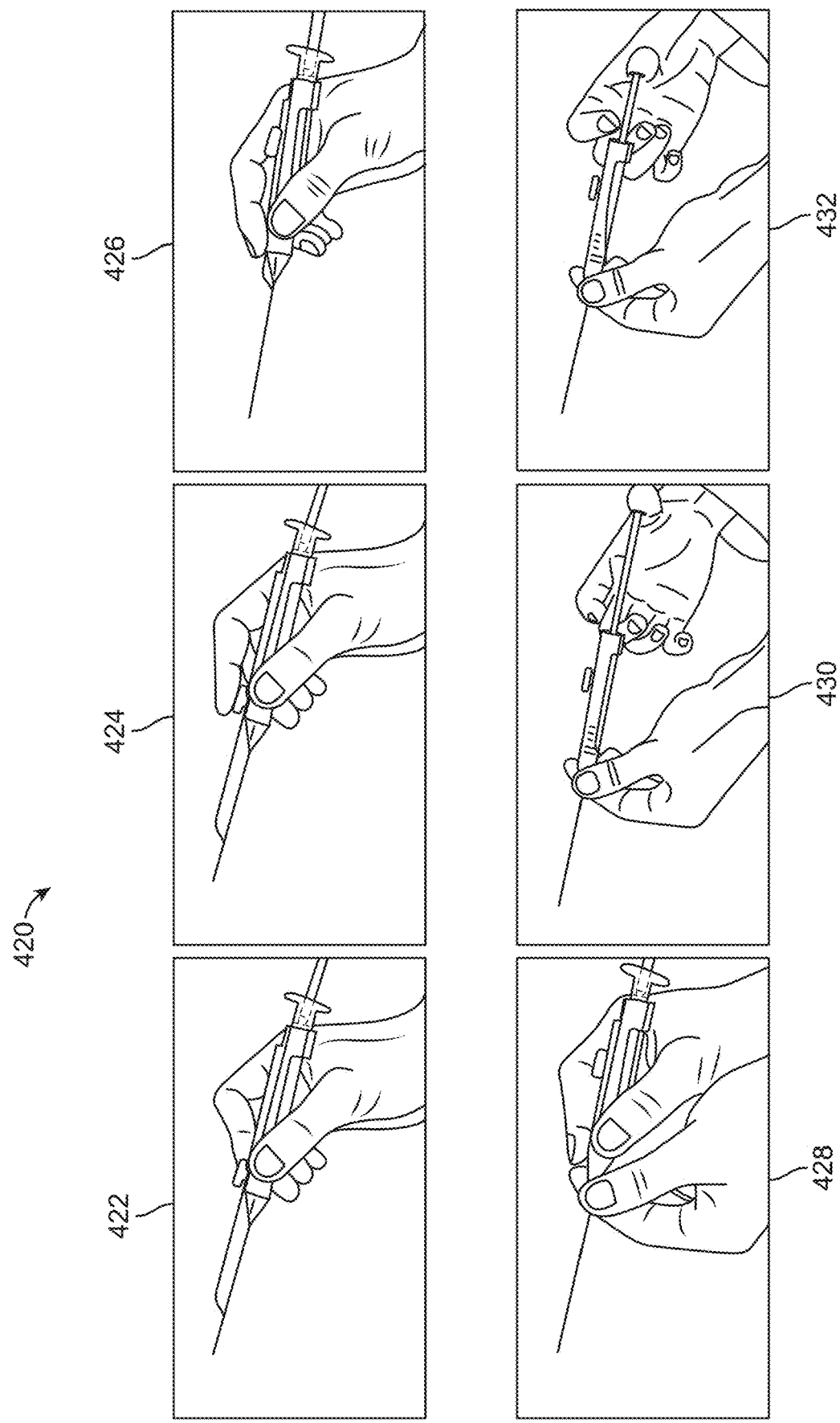
FIG. 35 is a multi-panel illustration of a method of performing an injection, using a needle and cannula device of the present disclosure, according to an alternative embodiment.

Referring now to FIG. 35, another embodiment of an injection method 420 is illustrated. This embodiment is similar to the one described immediately above, with a slightly different needle and cannula device. In the first illustrated step 422, the syringe has already been loaded into the needle and cannula device, and the needle has been advanced to the extended/distal position. Thus, the first illustrated step 422 is to introduce the needle into the skin. (No skin or model patient is shown in FIG. 35.) Indeed, in some embodiments, the syringe may come preloaded into the syringe holder. Although unlikely for safety reasons, the needle and cannula device may also come packaged in the needle-extended position. More likely, the needle will be packaged and shipped with the needle docked in the protected position within the needle guard. After the needle and the distal end of the cannula are inserted into the skin, the second step 424 involves pressing a needle carriage release button. In some embodiments, the needle may be retracted by pressing a button to cause the slider, support arm and needle to automatically retract. This may be achieved, for example, via a spring loaded mechanism within the syringe holder. The third illustrated step 426 is the needle auto-retracting into the needle guard/housing. The fourth step 428 is to stabilize the cannula, relative to the patient. Next, in the fifth step 430, the user may reposition his hand, if desired, to be able to advance the cannula and/or for a better position for completing the injection. Finally, in step six 432, the user presses the syringe plunger to inject the substance. When the injection is complete, the user removes the cannula from the patient.

FIGS. 36A-41 illustrate several alternative embodiments of a needle and cannula device for injections. Although each embodiment includes different shapes, configurations, parts and features, any embodiment described in this application may include shapes, configurations, parts and/or features described in relation to other embodiments. For example, just because one particular feature is not described for one particular embodiment, it does not mean that that embodiment cannot include that feature. Parts, features and overall shapes and configurations for various embodiments are interchangeable in this disclosure.

With reference now to FIGS. 36A and 36B, one embodiment of a needle and cannula device 450 is illustrated. The device 450 includes a syringe holder 452, a needle carriage 454, a needle 466 and a cannula 464. A syringe 470 is a separate component that is shown here for illustrative purposes. The needle carriage 454 has a proximal portion that wraps around the syringe holder 452, a finger stop feature 456, and a support arm 468 that attaches distally to the needle 466 (not visible in FIG. 36A, because retracted into the syringe holder 452). The syringe holder 452 includes proximal and distal needle carriage detents for locking the needle carriage 454 in the proximal/retracted and distal/extended positions. FIG. 36A shows the needle and cannula device 450 in the retracted position. FIG. 36B illustrates movement of the needle carriage 454 from the retracted position (solid lines) to the extended position (dotted lines).

With reference now to FIGS. 37A-37C, an alternative embodiment of a needle and cannula device 480 is illustrated. The device 480 includes a syringe holder 482, a needle carriage 483, a needle 486 and a cannula 484. A syringe 492 is a separate component that is shown here for illustrative purposes. The needle carriage 483 has a proximal portion 494 that wraps around the syringe 492, a finger slider 490 (or "thumb slider"), and a support arm 488 that attaches distally to the needle 486 (not visible in FIG. 37A, because retracted into the syringe holder 482). FIG. 37A shows the needle and cannula device 480 in the retracted position. FIG. 37B illustrates movement of the needle carriage 483 from the retracted position (solid lines) to the extended position (dotted lines). FIG. 37C is an end-on, cross sectional view showing the barrel of the syringe 492 enclosed within the wrap-around proximal portion 494 and the finger slider 490.

With reference now to FIGS. 38A and 38B, another alternative embodiment of a needle and cannula device 500 is illustrated. The device 500 includes a syringe holder 502, a needle carriage 506, a needle 516, a cannula 510, an extension spring 508 and a needle carriage release button 504. A syringe 512 is a separate component that is shown here for illustrative purposes. The needle carriage 506 is coupled at a proximal end to the extension spring 508, which advances the needle carriage 506 to the extended position (FIG. 38B) when the button 504 is pressed. The needle carriage 506 also includes a support arm 514 that connects distally with the needle 516. The needle carriage 506 may also include a textured finger grip portion 507, which the user may grasp to pull back the needle carriage 506 to the retracted position. FIG. 38A shows the needle and cannula device 500 in the retracted position, with the needle 516 housed in the syringe holder 502 and thus not visible. FIG. 38B shows the needle and cannula device 500 in the extended position.

Figure 39:
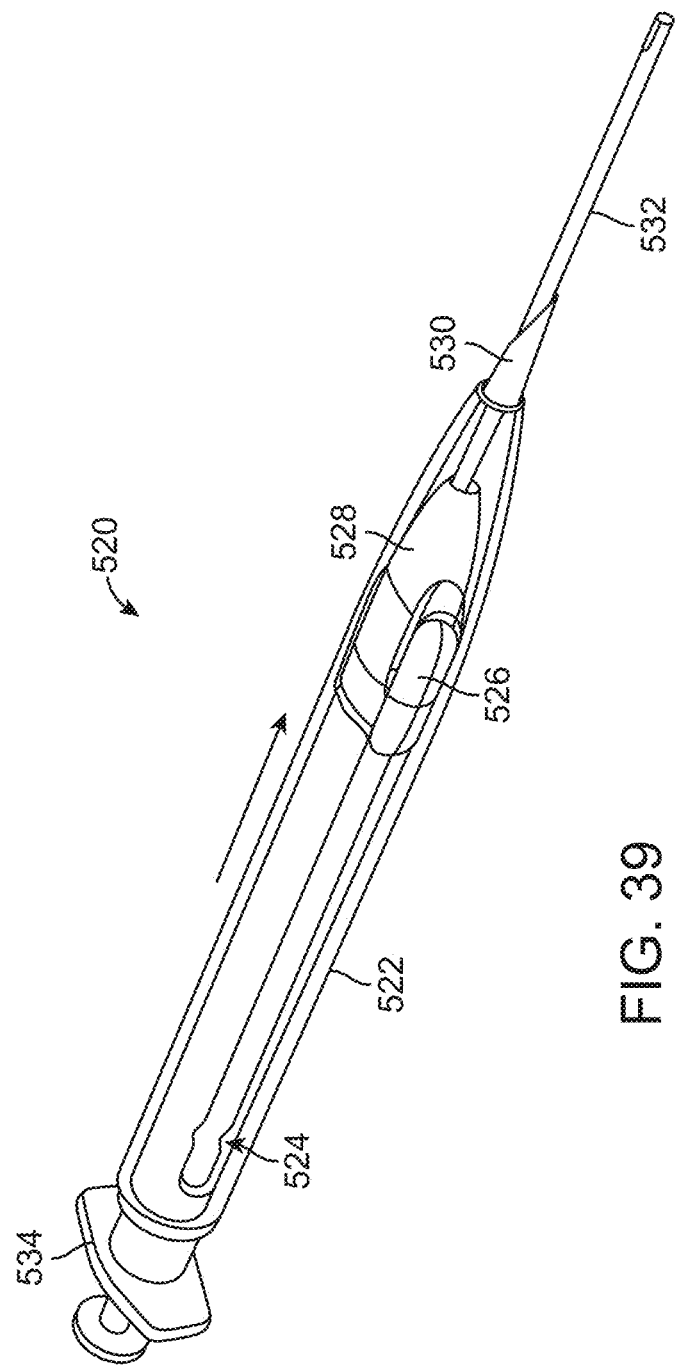
FIG. 39 is a perspective view of a needle and cannula device for performing injections, according to another alternative embodiment.

With reference now to FIG. 39, another alternative embodiment of a needle and cannula device 520 is illustrated. The device 520 includes a syringe holder 522, a needle carriage 528, a needle 530, a cannula 532, a positional needle carriage detent 524 and a release button 526. The release button 526 releases the needle carriage 528 to allow it to advance forward to the extended position. In this embodiment, as in all embodiments, the syringe holder 522 and/or any other part(s) of the needle and cannula device 520 may be made of a completely or partially transparent material, such as plastic or glass, to allow the user to easily view the barrel of the syringe 534 and the fluid level therein.

Figure 40:
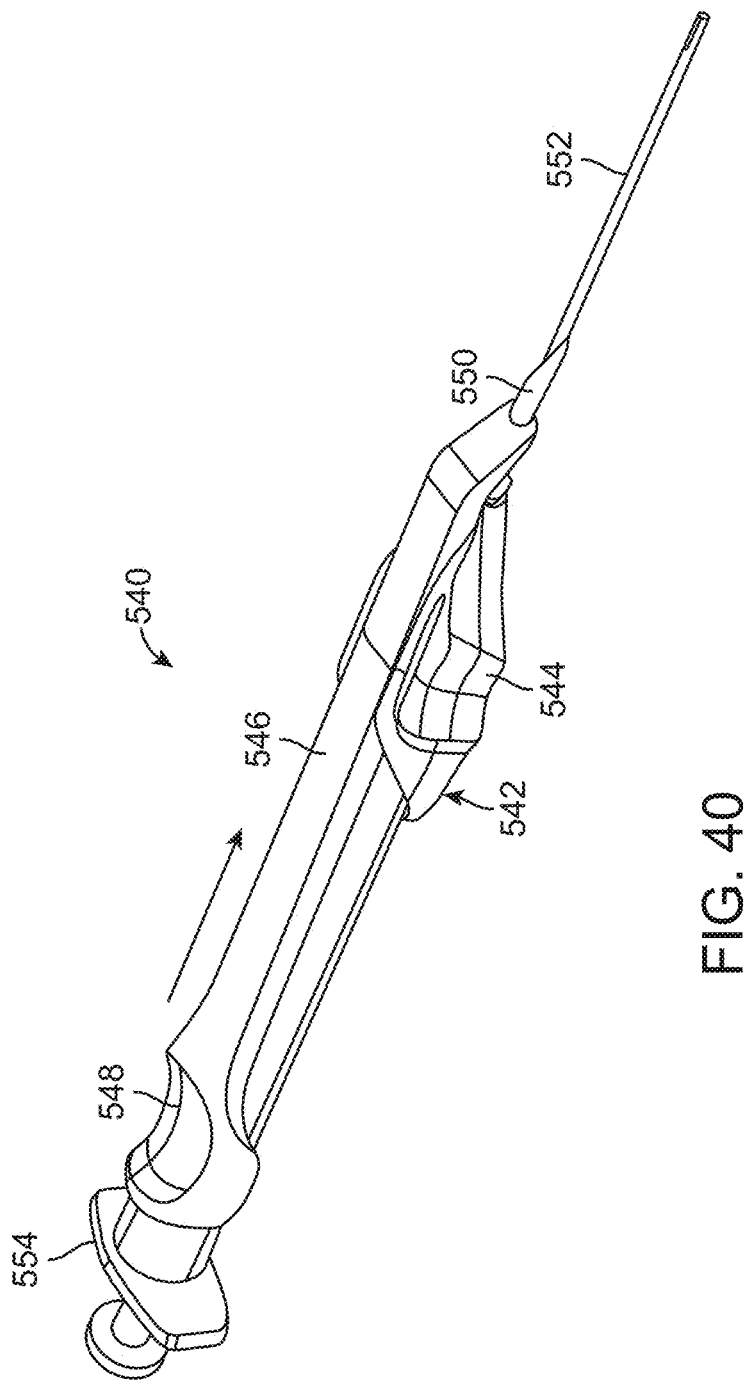
FIG. 40 is a perspective view of a needle and cannula device for performing injections, according to another alternative embodiment.

With reference now to FIG. 40, another alternative embodiment of a needle and cannula device 540 is illustrated. The device 540 includes a syringe holder 542, a needle carriage 546, a needle 550, and a cannula 552. The syringe holder 542 includes a release button 544 for releasing the needle carriage 546, which includes a thumb recess 548 for allowing the user to manually advance and/or retract the needle carriage 546. The syringe 554 is a separate device, shown for illustrative purposes.

Figure 41:
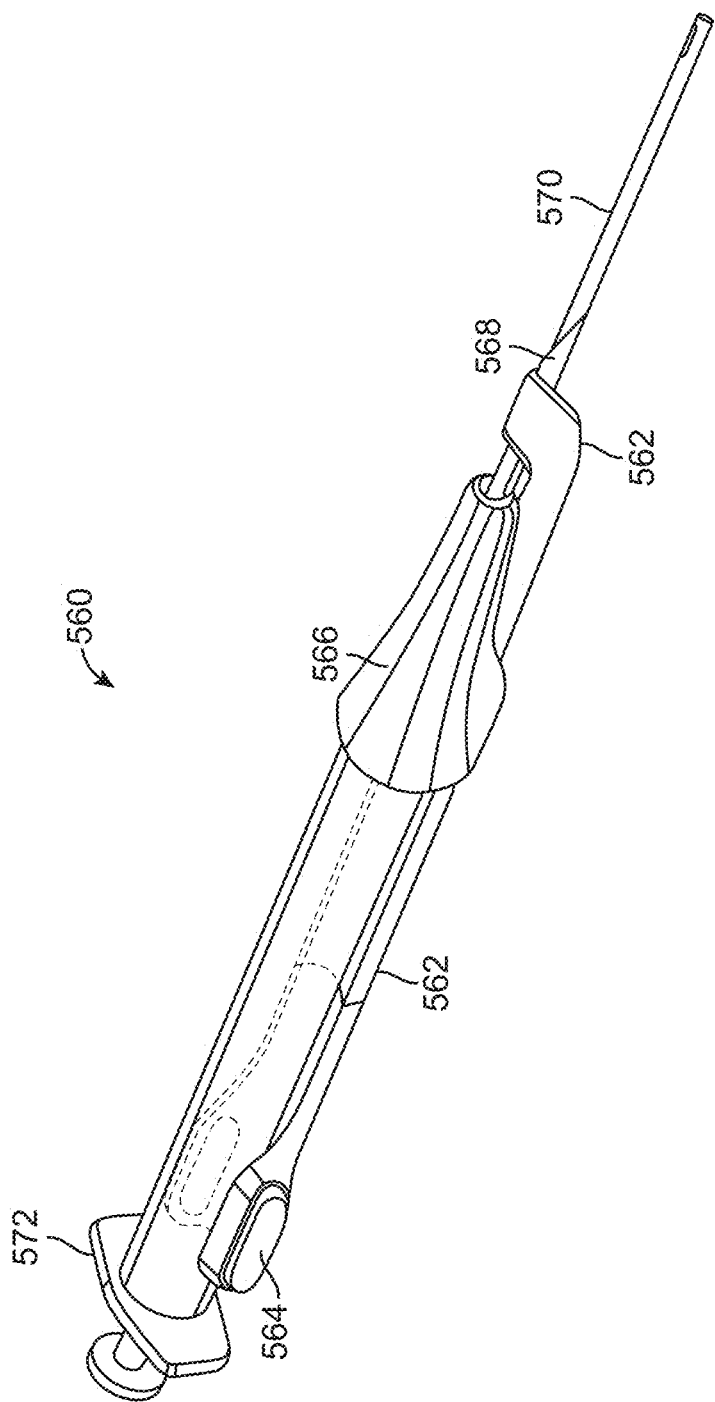
FIG. 41 is a perspective view of a needle and cannula device for performing injections, according to another alternative embodiment.

Referring now to FIG. 41, another alternative embodiment of a needle and cannula device 560 is illustrated. The device 560 includes a syringe holder 566, a needle carriage 562, a needle 568, and a cannula 570. A syringe 572 is shown for illustrative purposes. The needle carriage 562 includes a pinch release button 564 for releasing the needle carriage 542 to allow it to advance the needle.

Figure 42A:
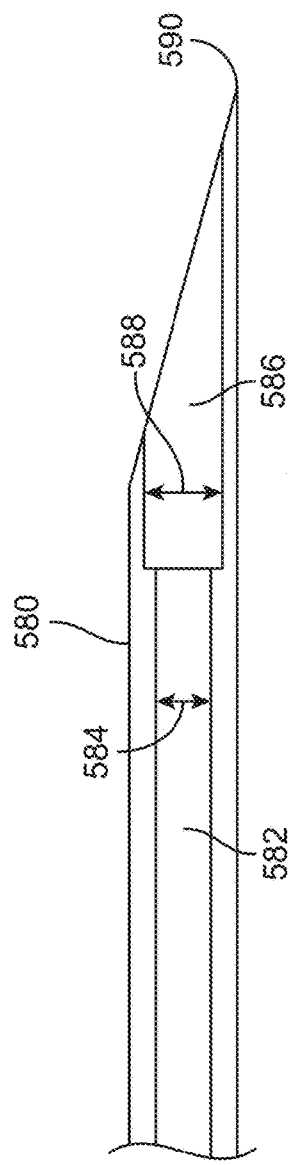
FIG. 42A is a side cross-sectional view of a needle with a larger inner diameter in a distal portion, according to one embodiment.
Figure 42B:
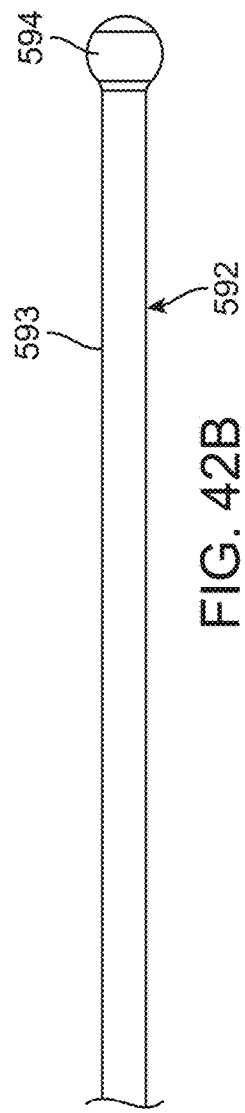
FIG. 42B is a side view of a ball-tipped cannula for use with the needle of FIG. 42B.
Figure 42C:
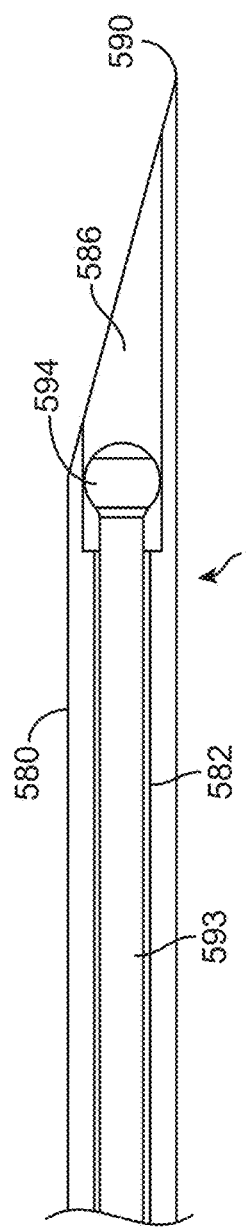
FIG. 42C is a side cross-sectional view of the needle of FIG. 42A with the ball-tipped cannula of FIG. 42B residing inside the needle.

Referring now to FIGS. 42A-42C, FIG. 42A is a side cross-sectional view of a needle 580 with a sharp tip 590, a proximal inner bore 582 having a first diameter 584 and a distal inner bore 586 having a second diameter 588 that is larger than the first diameter 584. The larger distal inner bore 586 is sized to accommodate a ball tip of a cannula. FIG. 42B is a side view of one embodiment of such a ball-tipped cannula 592, which has a shaft 593 and a ball tip 594. FIG. 42C is a side cross-sectional view of the needle 580 of FIG. 42A with the ball-tipped cannula 592 of FIG. 42B residing inside the needle 580. Together, the needle 580 and the ball-tipped cannula 592 make up a needle and cannula device 596. The ball tip 594 of the ball-tipped cannula 592 may help reduce trauma and unwanted cutting or piercing of tissue by the distal end of the cannula 592 and thus may facilitate an atraumatic, minimally invasive injection procedure. In various embodiments, the ball tip 594 may have different shapes, such as but not limited to a sphere, an elliptical shape, a football shape, a tapered shape or the like.

In all of the above-described embodiments, the syringe has been mentioned as a separate device, provided separately from and not included as part of the needle and cannula device. This is true for many embodiments, and in fact any given embodiment of the needle and cannula device may be configured for use with multiple different types and/or sizes of syringes, or may be adapted for use with different types and/or sizes of syringes. In some embodiments, different sizes of the needle and cannula device may be available, so that a user can select a size depending on what size of syringe is being used. In other embodiments, the needle and cannula device may actually include the syringe, so that the entire injection system is sold as one unit together. This may be advantageous, for example, for a company that produces and sells one or more dermal fillers or other injectable substances. Therefore, in any given embodiment, the needle and cannula device may include the syringe or may be provided separately from the syringe. Thus, the scope of this disclosure should not be limited either way.

Although the above description is believed to be complete and accurate, various changes to any of the embodiments and features described herein may be made, without departing from the scope of the invention.

We claim:

1. A device for performing injections in a patient, the device comprising:
    a syringe holder, comprising:
        a cone-shaped needle guard comprising a housing on a distal end of the syringe holder; and
        a track comprising a proximal end with a proximal locking feature and a distal end with a distal locking feature;
    a cannula extending from the cone-shaped needle guard of the syringe holder, wherein the cannula comprises a blunt tip and a cannula length;
    a needle slidably disposed over the cannula, wherein the needle comprises a sharp tip and a needle length that is shorter than the cannula length; and
    a needle carriage portion mounted on the track of the syringe holder, the needle carriage portion comprising:
        a slider; and
        a rigid support arm extending from the slider and including a needle attachment portion at its distal end that is coupled with the needle,
    wherein the slider is configured to release from the proximal locking feature in the track, slide distally along the track, and lock in the distal locking feature, thus moving the needle out of the cone-shaped needle guard and to an extended position, in which the sharp tip of the needle immediately adjacent the blunt tip of the cannula for piercing skin of the patient, and
    wherein the slider is further configured to release from the distal locking feature, slide proximally along the track, and lock in the proximal locking feature, thus moving the needle along the cannula from the extended position to a retracted position, in which the sharp tip is housed within the cone-shaped needle guard of the syringe holder.

2. The device of claim 1, further comprising a release mechanism on the slider for unlocking the slider from the distal locking feature or the proximal locking feature to allow the slider to slide along the track.

3. The device of claim 2, wherein the release mechanism comprises a button.

4. The device of claim 1, wherein the slider comprises:
    a proximal finger stop feature; and
    a distal finger stop feature.

5. The device of claim 1, wherein the syringe holder comprises a Luer lock for coupling with a syringe to place a barrel of the syringe in fluid communication with the cannula.

6. The device of claim 1, wherein at least part of the syringe holder is transparent, so that a user of the device can read markings on a syringe through the syringe holder.

7. The device of claim 1, wherein the syringe holder comprises a cylinder into which a syringe is inserted for use.

8. The device of claim 1, wherein the syringe holder comprises an open side into which a syringe is inserted for use.

9. The device of claim 1, further comprising a cannula hub attached to a proximal end of the cannula and housed within the housing.

10. The device of claim 1, wherein the slider is configured to slide a distance of between 40 mm and 50 mm from the extended position to the retracted position.

11. The device of claim 1, wherein the syringe holder has a length of between 115 millimeters and 120 millimeters.

12. The device of claim 1, wherein the cannula length is between 30 millimeters and 45 millimeters.

13. The device of claim 1, further comprising an automatic needle retraction mechanism coupled with the syringe holder and the slider, to automatically retract the needle into the cone-shaped needle guard.

* * * * *